US010311163B2

(12) United States Patent
MohammadBagher et al.

(10) Patent No.: US 10,311,163 B2
(45) Date of Patent: Jun. 4, 2019

(54) NON-PARAMETRIC MICROFACET FACTOR MODELS FOR ISOTROPIC BIDIRECTIONAL REFLECTANCE DISTRIBUTION FUNCTIONS

(71) Applicant: Microsoft Technology Licensing, LLC, Redmond, WA (US)

(72) Inventors: Mahdi MohammadBagher, Montreal (CA); Derek Nowrouzezahrai, Montreal (CA); John Michael Snyder, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 949 days.

(21) Appl. No.: 14/320,636

(22) Filed: Jun. 30, 2014

(65) Prior Publication Data
US 2015/0379162 A1    Dec. 31, 2015

(51) Int. Cl.
*G01N 21/55*    (2014.01)
*G06F 17/50*    (2006.01)
*G06T 15/50*    (2011.01)

(52) U.S. Cl.
CPC ............. *G06F 17/50* (2013.01); *G01N 21/55* (2013.01); *G06T 15/506* (2013.01)

(58) Field of Classification Search
CPC ....................................................... G06F 17/50
USPC ........................................................ 345/426
See application file for complete search history.

(56) References Cited

U.S. PATENT DOCUMENTS

| 6,803,910 | B2 | 10/2004 | Pfister et al. |
| 8,953,037 | B2 | 2/2015 | Wang et al. |
| 2006/0143142 | A1 | 6/2006 | Vasilescu et al. |
| 2010/0277477 | A1* | 11/2010 | Wang .................. G06T 15/506 345/426 |
| 2013/0093883 | A1 | 4/2013 | Wang et al. |

FOREIGN PATENT DOCUMENTS

| RU | 2305320 C2 | 8/2007 |
| WO | 2016003747 A2 | 1/2016 |

OTHER PUBLICATIONS

Lawrence, Jason et al. "Inverse Shade Trees for Non-Parametric Material Representation and Editing". ACM Transactions on Graphics 25.3 (2006): 735.*
Ben-Artzi, Aner, Ryan Overbeck, and Ravi Ramamoorthi. "Real-Time BRDF Editing in Complex Lighting". ACM Transactions on Graphics 25.3 (2006): 945.*
Michael Ashikmin, Simon Premože, and Peter Shirley. 2000. A microfacet-based BRDF generator. In Proceedings of the 27th annual conference on Computer graphics and interactive techniques (SIGGRAPH '00). ACM Press/Addison-Wesley Publishing Co., New York, NY, USA, 65-74.*
Smith, Bruce, G., "Geometrical Shadowing of a Random Rough Surface", in Proceedings of IEEE Transactions on Antennas and Propagation, vol. 15, Issue 5, Sep. 1967, pp. 668-671.

(Continued)

*Primary Examiner* — Shivang I Patel
(74) *Attorney, Agent, or Firm* — Rainier Patents, P.S.

(57) ABSTRACT

A plurality of measured sample data points associated with reflectance on a surface of a material is obtained. A non-parametric densely tabulated one-dimensional representation for a plurality of factors in a microfacet model is generated, using the obtained sample data points.

20 Claims, 11 Drawing Sheets

(56) References Cited

OTHER PUBLICATIONS

Stam, Jos, "An Illumination Model for a Skin Layer Bounded by Rough Surfaces", in Proceedings of the 12th Eurographics conference on Rendering, Jun. 25, 2001, pp. 1-22.
Steigleder, et al., "Factorization of the Ashikhmin BRDF for Real-time Rendering", in Journal of Graphics Tools—Special on hardware-accelerated rendering techniques, vol. 7, Issue 4, Dec. 1, 2002, 1 page.
Tofallis, et al., "Least Squares Percentage Regression", in Journal of Modern Applied Statistical Methods, vol. 7, No. 2, Nov. 2008, pp. 526-534.
Torrance, et al., "Theory for Off Specular Reflection from Roughened Surfaces", in Journal of the Optical Society of America, vol. 57, No. 9, Sep. 1967, pp. 1105-1114.
Tsai, et al., "All-Frequency Precomputed Radiance Transfer using Spherical Radial basis Functions and Clustered Tensor Approximation", in Journal of ACM Transactions on Graphics, vol. 25, Issue 3, Jul. 2006, 10 pages.
Walter, et al., "Microfacet Models for Refraction through Rough Surfaces", in Proceedings of the 18th Eurographics Conference on Rendering Techniques, Jun. 25, 2007, 12 pages.
Wang, et al., "Efficient Wavelet Rotation for Environment Map Rendering", in Proceedings of the 17th Eurographics Conference on Rendering Techniques, Jun. 26, 2006, 10 pages.
Wang, et al., "All-Frequency Rendering of Dynamic, Spatially-Varying Reflectance", in Proceedings of ACM SIGGRAPH, Dec. 17, 2009, 10 pages.
Ward, Gregory J., "Measuring and Modeling Anisotropic Reflection", in Proceedings of Computer Graphics, vol. 26, Issue 2, Jul. 1992, 8 pages.
Weidlich, et al., "Arbitrarily Layered Micro-Facet Surfaces", in Proceedings of the 5th International Conference on Computer Graphics and Interactive Techniques in Australia and Southeast Asia, Dec. 1, 2007, 8 pages.
White, Halbert, "A Heteroskedasticity-Consistent Covariance Matrix Estimator and a Direct Test for Heteroskedasticity", in Proceedings of Econometrica, vol. 48, No. 4, May 1980, 23 pages.
"International Search Report & Written Opinion Issued in PCT Application No. PCT/US2015/037566", dated Jun. 8, 2016, 23 Pages.
Shi, et al., "A Biquadratic Reflectance Model for Radiometric Image Analysis", in Proceedings of the IEEE Conference on Computer Vision and Pattern Recognition, Jun. 16, 2012, pp. 230-237.
Susaki, et al., "Robust Estimation of BRDF Model Parameters", in Journal-Remote Sensing of Environment, vol. 89, Issue 1, Jan. 15, 2004, pp. 63-71.
Zhang, Zhengyou, "Parameter Estimation Techniques: A Tutorial with Application to Conic Fitting", in Journal-Image and Vision Computing, vol. 15, Issue 1, Jan. 1997, pp. 59-76.
Ruiters, et al., "A Compact and Editable Representation for Measured BRDF", in Computer Graphics Technical Report CG-2010-1, Dec. 2010, 11 Pages.
Mahdi M. Bager, et al., "A Non-Parametric Factor Microfacet Model for Isotropic BRDFs," ACM Transactions on Graphics (TOG), vol. 35, No. 5, article 159, Jul. 28, 2016, 16 pages.
Tsai et al., "Importance sampling of products from illumination and BRDF using spherical radial basis functions", Journal of Visual Computer, vol. 24, Issue 7, May 29, 2008, 10 pages.
Demand filed Sep. 8, 2016 with Response to the International Search Report & Written Opinion dated Jun. 8, 2016 from PCT Patent Application No. PCT/US2015/037566, 16 pages.
Communication pursuant to Rules 161(1) and 162 EPC dated Feb. 7, 2017 from European Patent Application No. 15739088.1, 2 pages.
Response filed Mar. 13, 2017 to the Communication pursuant to Rules 161(1) and 162 EPC dated Feb. 7, 2017 from European Patent Application No. 15739088.1, 20 pages.
Yong, et al., "Modeling and Editing Isotropic BRDF", in Proceedings of Second International Conference on Modeling, Simulation and Visualization Methods, May 15, 2010, 4 pages.

Alldrin, et al., "Photometric Stereo with Non-Parametric and Spatially-Varying Reflectance", in IEEE Conference on Computer Vision and Pattern Recognition, Jun. 23, 2008, 8 pages.
Pacanowski, et al., "Rational BRDF", in Proceedings of IEEE Transactions on Visualization and Computer Graphics, vol. 18, Issue 11, Nov. 2012, 13 pages.
Zickler, et al., "Reflectance Sharing: Predicting Appearance from a Sparse Set of Images of a Known Shape", in IEEE Transactions on Pattern Analysis and Machine Intelligence, vol. 28, No. 8, Aug. 2006, 16 pages.
Wang, et al., "Modeling Anisotropic Surface Reflectance with Example-Based Microfacet Synthesis", in Proceedings of ACM SIGGRAPH, vol. 27, Issue 3, Aug. 2008, 9 pages.
Nishino, Ko, "Directional Statistics BRDF Model", in Proceedings of 12th International Conference on Computer Vision, Sep. 29, 2009, 8 pages.
Stark, et al., "Barycentric Parameterizations for Isotropic BRDFs", in Proceedings of IEEE Transactions on Visualization and Computer Graphics, vol. 11, No. 2, Mar. 2005, pp. 126-138.
Shi, et al., "Bi-polynomial Modeling of Low-frequency Reflectances", in Proceedings of IEEE Transactions on Pattern Analysis and Machine Intelligence, Oct. 3, 2013, pp. 1-14.
Rusinkiewicz, Szymon M., "A New Change of Variables for Efficient BRDF Representation", in Proceedings of Eurographics Workshop on Rendering, Jun. 29, 1998, 12 pages.
Chen, et al., "Modeling and Simulation of BRDF of Typical Targets", in Proceedings of Symposium on Photonics and Optoelectronics, May 16, 2011, 4 pages.
Cook, et al., "A reflectance model for computer graphics", in Journal ACM Transactions on Graphics, vol. 1, Issue 1, Jan. 1982, pp. 7-24.
McCool, et al., "Homomorphic factorization of BRDFs for high-performance rendering", in Proceedings of the 28th Annual Conference on Computer Graphics and Interactive Techniques, Aug. 12, 2001, pp. 171-178.
Ngan, et al., "Experimental Analysis of BRDF Models", in Proceedings of the Eurographics Symposium on Rendering Techniques, Jun. 29, 2005, 11 pages.
Lawrence, et al., "Inverse shade trees for non-parametric material representation and editing", in Proceedings of ACM SIGGRAPH, Jul. 30, 2006, pp. 735-745.
Ashikhmin, et al., "Distribution-based BRDFs", in Technical Report, Jun. 27, 2014, 10 pages.
Ashikhmin, et al., "A Microfacet-based BRDF Generator ", in Proceedings of the 27th annual conference on Computer graphics and interactive techniques, Jul. 1, 2000, 10 pages.
Bilgili, et al., "A General BRDF Representation Based on Tensor Decomposition", in Proceedings of Computer Graphics Forum, vol. 30, No. 8, Dec. 2011, pp. 2427-2439.
Blinn, James F., "Models of light reflection for computer synthesized pictures", in Proceedings of the 4th annual conference on Computer graphics and interactive techniques, Jul. 20, 1977, pp. 192-198.
Bourlier, et al., "One- and Two-Dimensional Shadowing Functions for any Height and Slope Stationary Uncorrelated Surface in the Monostatic and Bistatic Configurations", in IEEE Transactions on Antennas and Propagation, vol. 50, Issue 3, Mar. 2002, pp. 312-324.
Brown, Gary S., "Shadowing by non-Gaussian random surfaces", in IEEE Transactions on Antennas and Propagation, vol. 28, Issue 6, Nov. 1980, pp. 788-790.
Burley, Brent, "Physically-Based Shading at Disney", in Proceedings of 39th International Conference and Exhibition on Computer Graphics and Interactive Techniques, Aug. 5, 2012, 26 pages.
Chandrasekhar, Subrahmanyan, "Radiative Transfer", in Publication of Dover Books, Jun. 30, 2014, 3 pages.
"Method 8000C", Published on: Mar. 2003, Available at: http://www.epa.gov/osw/hazard/testmethods/pdfs/8000c_v3.pdf.
Graybill, et al., "Regression Analysis: Concepts and Applications", in Publication Duxbury Press, Jan. 1994, 3 pages.
Jarosz, et al., "Importance sampling spherical harmonics", in Proceedings of Eurographics, vol. 28, No. 2, Apr. 2, 2009, 10 pages.

(56) References Cited

OTHER PUBLICATIONS

Kajiya, James T., "The Rendering Equation", in Proceedings of the 13th annual conference on Computer graphics and interactive techniques, Aug. 18, 1986, pp. 143-150.

Kautz, et al., "Interactive Rendering with Arbitrary BRDFs using Separable Approximations", in Proceedings of the 10th Eurographics conference on Rendering, Jun. 21, 1999, 15 pages.

Kautz, et al., "Fast, arbitrary BRDF shading for low-frequency lighting using spherical harmonics", in Proceedings of the 13th Eurographics workshop on Rendering, Jul. 26, 2002, 7 pages.

Kolda, et al., "Tensor Decompositions and Applications", in Journal SIAM Review, vol. 51, Issue 3, Aug. 2009, 46 pages.

Kurt, et al., "An anisotropic BRDF model for fitting and Monte Carlo rendering", in Proceedings of ACM SIGGRAPH Computer Graphics—Visual Research, Evaluation and Assessment in the Age of Computer Graphics, vol. 44, Issue 1, Feb. 2010, 15 pages.

Lafortune, et al., "Non-linear approximation of reflectance functions", in Proceedings of the 24th annual conference on Computer graphics and interactive techniques, Aug. 3, 1997, 10 pages.

Lawrence, et al., "Efficient BRDF Importance Sampling Using a Factored Representation", in Proceedings of ACM SIGGRAPH, vol. 23, Issue 3, Aug. 2004, pp. 496-505.

Lawrence, et al., "Inverse Shade Trees for Non-Parametric Material Representation and Editing", in Proceedings of ACM Transactions on Graphics, vol. 25, No. 3, Jul. 2006, 13 pages.

Lazanyi, et al., "Fresnel Term Approximations for Metals", in Proceedings of 13th International Conference in Central Europe on Computer Graphics, Visualization and Computer Vision, Jan. 31, 2005, 4 pages.

Low, et al., "BRDF Models for Accurate and Efficient Rendering of Glossy Surfaces", in Journal of ACM Transactions on Graphics, vol. 31, Issue 1, Jan. 2012, pp. 1-14.

Ma, et al., "Real-Time Triple Product Relighting Using Spherical Local-frame Parameterization", in Proceedings of the Visual Computer, vol. 22, Nos. 9-11, Sep. 2006, pp. 1-10.

Marschner, et al., "Image Based BRDF Measurement Including Human Skin", in Proceedings of the 10th Eurographics conference on Rendering, Jun. 21, 1999, pp. 1-15.

Matusik, et al., "A Data-driven Reflectance Model", in Proceedings of ACM SIGGRAPH, Jul. 27, 2003, 11 pages.

McAuley, et al., "Practical Physically-based Shading in Film and Game Production", in Proceedings of ACM SIGGRAPH, Aug. 5, 2012, 7 pages.

Ngan, et al., "Experimental Analysis of BRDF Models", in Proceedings of the Sixteenth Eurographics Conference on Rendering Techniques, Jun. 2005, 13 pages.

Oren, et al., "Generalization of Lambert's Reflectance Model", in Proceedings of the 21st Annual Conference on Computer Graphics and Interactive Techniques, Jul. 24, 1994, 15 pages.

Poulin, et al., "A Model for Anisotropic Reflection", in Proceedings of ACM SIGGRAPH Computer Graphics, vol. 24, Issue 4, Aug. 1990, pp. 273-282.

Press, et al., "Numerical Recipes 3rd Edition: The Art of Scientific Computing", Published on: Oct. 9, 2007 Available at: http://www.researchgate.net/publication/234831331_Numerical_Recipes_3rd_Edition_The_Art_of_Scientific_Computing.

Ramamoorthi, et al., "An Efficient Representation for Irradiance Environment Maps", in Proceedings of the 28th Annual Conference on Computer Graphics and Interactive Techniques, Aug. 12, 2001, pp. 497-500.

Schlick, Christophe, "An Inexpensive BRDF Model for Physically Based Rendering", in Proceedings of Computer Graphics Forum, vol. 13, No. 3, Sep. 12, 1994, 15 pages.

Sloan, et al., "Precomputed Radiance Transfer for Real-time Rendering in Dynamic, Low Frequency Lighting Environments", in Journal of ACM Transactions on Graphics, vol. 21, Issue 3, Jul. 2002, pp. 527-536.

Ben-Artzi, et al., "Real-Time BRDF Editing in Complex Lightings", in Proceedings of 33rd International Conference and Exhibition on Computer Graphics and Interactive Techniques, Jul. 30, 2006, 10 pages.

Bagher, et al., "Accurate Fitting of Measured Reflectances using a Shifted Gamma Micro-Facet Distribution", in Proceedings of 23rd Eurographics Symposium on Rendering, vol. 31, Issue 4, Jun. 2012, 10 pages.

"Volume Form", Retrieved on: Dec. 30, 2013, Available at: http://en.wikipedia.org/wiki/Volume_form.

"Metric Tensor", Retrieved on: Dec. 30, 2013, Available at: http://en.wikipedia.org/wiki/Metric_tensor.

"International Preliminary Report on Patentability Issued in counterpart PCT Application No. PCT/US2015/037566", dated Nov. 4, 2016, 7 Pages.

"Office Action Issued in Mexican Patent Application No. MX/a/2016/016735", dated Jul. 13, 2018, 3 Pages.

"Notice of Allowance Issued in Russian Patent Application No. 2016151177", dated Feb. 7, 2019, 16 pages.

\* cited by examiner

NON-PARAMETRIC MICROFACET FACTOR MODELS FOR ISOTROPIC BIDIRECTIONAL REFLECTANCE DISTRIBUTION FUNCTIONS

BACKGROUND

A material's BRDF (bidirectional reflectance distribution function) represents its reflectance, i.e., how it shadows and scatters light incident at a single point on its surface. In general, the BRDF is a four-dimensional (4D) function, depending on the direction of the light and the view relative to the surface normal vector. Many materials are isotropic, as their reflectance does not change if a flat uniform sample is rotated azimuthally around its normal vector. Isotropic materials can be parameterized by a three-dimensional (3D) rather than a 4D set of measurements. However, these tend to be substantially cumbersome representations, more particularly if reflectance varies spatially.

SUMMARY

According to one general aspect, a system may include an apparatus that includes a computer-readable storage medium storing executable code, the executable code including a reflectance representation manager that includes a data acquisition module that obtains a plurality of measured sample data points associated with reflectance on a surface of a material. A representation generator generates a non-parametric densely tabulated one-dimensional representation for a plurality of factors in a microfacet model, using the obtained sample data points.

According to another aspect, measured sample data points associated with reflectance on a surface of a material may be obtained. The measured sample data points may be fitted to a model by applying a model fitting metric to the obtained sample data points, the model fitting metric calculated using a nonnegative, nonzero power of a ratio of a first function and a second function, the first and second functions defined over normalized values of the plurality of measured sample data points, the first function defined as a compressive function, the second function defined as a non-asymptotically increasing function.

According to another aspect, measured sample data points associated with reflectance on a surface of a material may be obtained. The measured sample data points may be fitted to a model by applying a fitting metric to the obtained sample data points, the fitting metric calculated using a sum-of-squares weighting, the sum-of-squares weighting including a non-constant function of measurement magnitudes of the obtained plurality of measured sample data points.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. The details of one or more implementations are set forth in the accompanying drawings and the description below. Other features will be apparent from the description and drawings, and from the claims.

DRAWINGS

DETAILED DESCRIPTION

I. Introduction

In accordance with example techniques discussed herein, a general representation for the reflectance of isotropic materials may be based on a one-dimensional (1D) non-parametric tabulation of factor functions from a standard microfacet model in computer graphics. This model may provide an accurate and compact characterization of reflectance by reducing a three-dimensional (3D) dataset to a set of three tabulated 1D factors.

In this context, "isotropic" materials may generally refer to exhibiting properties (e.g., as velocity of light transmission) with the same values (or substantially the same values) when measured along axes in all directions, or having the identical values (or substantially identical values) of a property in all directions.

In this context, "tabulate" may generally refer to obtaining a set of samples based on determining sampled values of a function over a particular domain set. For example, for a function $y=f(x)$ defined over x in [0, 1], storing a tabulation would involve taking samples of x, and storing values of $f$ at those values of x (i.e., storing those values $f(x)$).

In accordance with example techniques discussed herein, such a model may be fitted to real-world measurements of isotropic materials via an alternating weighted least squares (AWLS) numerical technique. For example, each factor may be optimally updated in an iterated sequence while holding the rest of the factors constant. For example, the weights, which determine how each measured BRDF (bidirectional reflectance distribution function) sample contributes to overall error in the optimization objective, may be determined by the product of (1) the sample's parametric volume form, (2) its importance in the rendering integral, and (3) its expected measurement error. To obtain desirable BRDF fits that are useful in synthetic renderings, BRDF samples in the small but often very bright highlight regions of its parameter space may be down-weighted in this third weighting factor.

In accordance with example techniques discussed herein, non-parametric microfacet factor representations may be utilized for representations for the reflectance of isotropic materials.

In accordance with example techniques discussed herein, an alternating weighted least squares (AWLS) fitting method for a product of factors of known functional dependence with compressive weighting may also be utilized for reflectance representation. As discussed herein, the AWLS fitting method is an example technique for compact representation of HDR (high dynamic range) measured data, with application in many areas other than reflectance representation.

Figure 1:
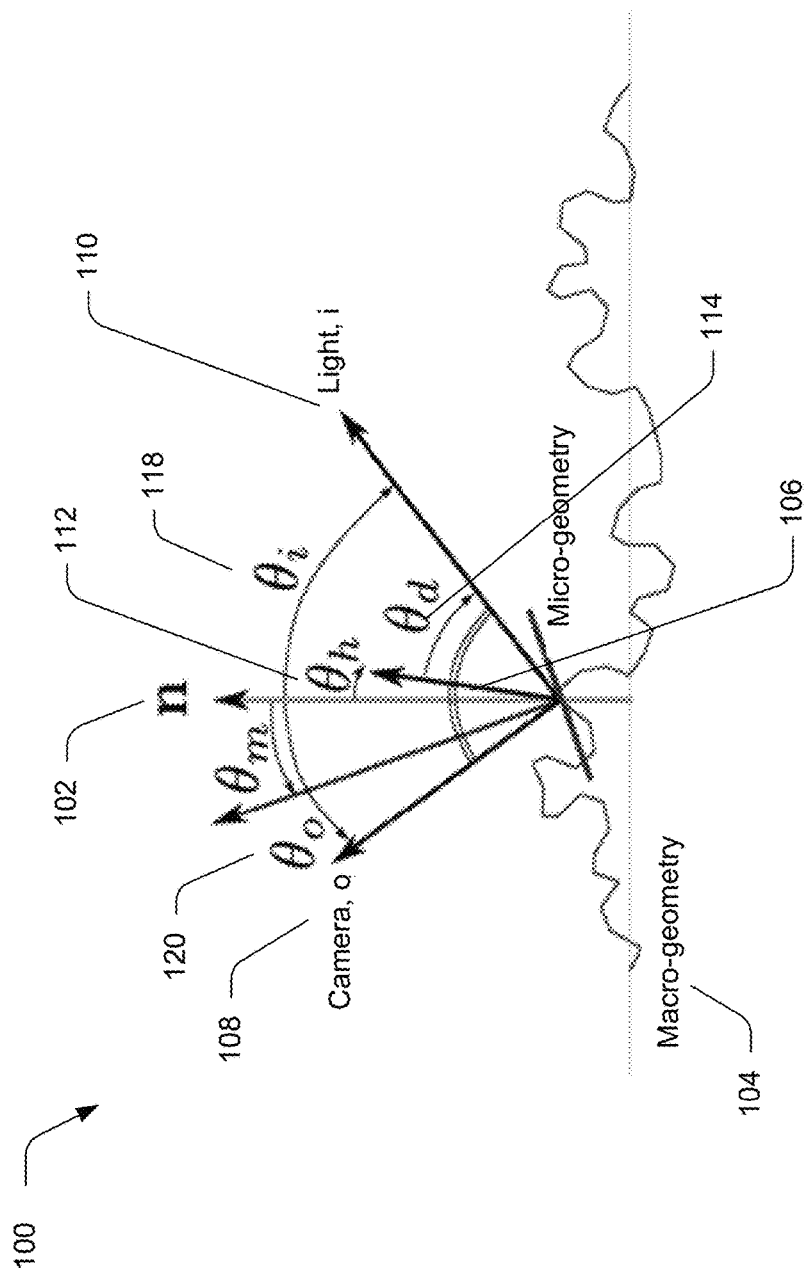
FIG. 1 depicts an example parameterization of an isotropic BRDF.

An isotropic BRDF may be parameterized in terms of three angles $$(\theta_h, \theta_d, \phi_d), \theta_h \in [0, \pi/2], \theta_d \in [0, \pi/2], \phi_d \in [0, \pi] \quad (1)$$

as shown in FIG. 1.

For example, as shown in the parameterization 100 of an isotropic BRDF of FIG. 1, a normal 102 to a surface macro-geometry 104 may be denoted n. A halfway vector h=(i+o)/||i+o|| is the vector 106 midway between a view (or camera) direction o (108) and a light direction i (110). $\theta_h$ denotes the angle 112 made between the halfway vector 106 and the normal vector 102; $\theta_d$ denotes the angle 114 made between the light vector 110 and the halfway vector 106 (which may also equal the angle between the view direction 108 and the halfway vector 106, since the halfway vector 106 is midway between the two directions). An angle $\phi_d$ (not shown) represents the rotation of the light vector i (110) and view vector o (108) around the halfway vector 106.

The angles made by the "in" (light) (118) and "out" (view) (120) directions with the (macro-scale) surface normal, $\theta_i \in [0, \pi/2]$ and $\theta_o \in [0, \pi/2]$, are determined from these basic parameters via the following formula:

$$\cos\theta_i = \cos\theta_h \cos\theta_d + \sin\theta_h \cos\phi_d \sin\theta_d$$

$$\cos\theta_o = \cos\theta_h \cos\theta_d - \sin\theta_h \cos\phi_d \sin\theta_d \quad (2)$$

An example non-parametric microfacet model may be indicated as:

$$\rho(\theta_h, \theta_d, \phi_d) = \rho_d + \rho_s \frac{D(\theta_h) F(\theta_d) G(\theta_i) G(\theta_o)}{\cos\theta_i \cos\theta_o} \quad (3)$$

which is a conventional model in computer graphics, introduced by Cook and Torrance in 1982 (see, e.g., Cook and Torrance, "A reflectance model for computer graphics," SIGGRAPH 1982). The factor D, which may be referred to as the normal distribution function or NDF, is a probability distribution function representing the probability that a microfacet normal makes an angle of $\theta_h$ with the surface macro-scale normal. The factor F, which may be referred to as the Fresnel factor, represents how reflectance depends on the "spread" angle $\theta_d$. The factor G, which may be referred to as the geometric factor, represents how the micro-geometry shadows and inter-reflects light onto itself, as a function of the obliquity of the light or view direction (i.e., on $\theta_i$, or $\theta_o$). The physical principle of reciprocity implies that reflectance is identical (or substantially identical) if the light and view direction are swapped (e.g., so the model may be symmetric in $\theta_i$, and $\theta_o$).

In accordance with example techniques discussed herein, the above model (Equation (3)) may be applied independently for each color channel of the measurement spectrum (e.g., 3-channel measurement for RGB (red-green-blue)).

Many previous techniques have assumed simple and limited analytic models for each of these factors. However, in accordance with example techniques discussed herein, a user may advantageously solve for the above factors without assuming any particular parametric model or analytic form for them. Example representations discussed herein sample each factor function at a set of (many) discrete samples of its input argument, treating it as a 1D vector, thus assuming the functional form of the microfacet model above, without restricting the form of its individual factors.

In accordance with example techniques discussed herein, an objective function F (e.g., a fitting metric) used to fit the above model may involve summing over all measured BRDF samples indexed j, indicated as:

$$F = \Sigma_j w_j (\rho(\theta_h, \theta_d, \phi_d)_j - \tilde{\rho}_j)^2 \quad (4)$$

wherein $\tilde{\rho}_j$ is the value of the j-th BRDF sample, corresponding to parametric coordinates $(\theta_h, \theta_d, \phi_d)_j$.

In accordance with example techniques discussed herein, a weighting $w_j$ at BRDF sample j may be indicated as shown by Equation (5):

$$w_j = w_V(\theta_h, \theta_d, \phi_d)_j w_I(\theta_h, \theta_d, \phi_d)_j w_E(\rho_j) \quad (5)$$

An example volume form may be indicated as:

$$w_V = \sin\theta_d \sqrt{(\cos^2\theta_d + \sin^2\theta_d \cos^2\phi_d)} d\theta_h d\theta_d d\phi_d \quad (6)$$

An example derivation for this formula is discussed further below.

An example importance weight $w_I$ may be indicated as:

$$w_I = \cos(\theta_i)\cos(\theta_o) \quad (7)$$

The factor $\cos(\theta_i)$ appears because the shaded result at any surface point seen from direction $\omega_o$ is given by the hemispherical integral over lighting directions $\omega_i$, indicated as:

$$s(\omega_o) = \int_{\omega_i \in \Omega} \rho(\omega_i, \omega_o) L(\omega_i) \cos\theta_i d\omega_i \quad (8)$$

wherein $L(\omega_i)$ represents incident radiance (lighting) in the direction $\omega_i$. The factor $\cos\theta_o$ arises due to surface points being more likely to appear as the normal aligns to the view direction.

An expected measurement error $w_E$ may be indicated as:

$$w_E = \left( \frac{f(\tilde{\rho}_j / \bar{\rho})}{\tilde{\rho}_j} \right)^p \quad (9)$$

wherein $f$ is an example "compressive function" of the form $$f(x) = \frac{1}{\alpha}(1 - e^{-\alpha x}) \quad (10)$$

and $\bar{\rho}$ is the weighted median of the BRDF, with weight given by $w_V w_I$. The weighting power p is a parameter that may be chosen in [1, 2]. The bigger the value of p, the higher weight is assigned to darker parts of the BRDF relative to its bright highlights. The form of this example compressive function has the advantageously desirable property that it maps to the finite interval [0, 1/α] as x ranges over all non-negative real numbers. The compressive function's α parameter may be selected, for example, as α=ln 2 in order to map the BRDF weighted median to the center of the output range (to ½α). The bigger the value of α, the more compressive the transformation is; i.e., the more high values are squeezed close to the function's asymptotic value of 1/α (thus the reference to "compressive"). The derivative of $f$ at x=0 is 1, so that the maximum ratio in the weight $w_E$ before raising it to the power p is indicated by:

$$\lim_{x \to 0} \frac{f(x)}{x} = 1 \quad (11)$$

From this maximum, the weighting ratio decreases monotonically to 0 as the BRDF value increases to ∞. In particular, this example formulation may advantageously substantially eliminate difficulty with weights becoming arbitrarily large as a measurement approaches a value of 0. This is not true of simpler weighting schemes where the numerator is chosen to be 1 rather than the compressive function.

In accordance with an example AWLS iteration, to solve for a factor, a user may hold everything but that factor constant, and may then solve for its optimal weighted least-squares update. Each component in the factor's tabulation may be solved for independently, based on the following observation.

Given the objective function:

$$F(x) = \Sigma_j w_j (z_j - x y_j)^2 \tag{12}$$

the solution for x that minimizes F may be indicated as:

$$x = \frac{\Sigma_j w_j y_j z_j}{\Sigma_j w_j y_j^2} \tag{13}$$

All samples may thus be accumulated that map to a given tabulated "bin" of the factor, applying the above formula (Equation (13)) in each bin.

To solve for $\rho_s$ and $\rho_d$, it may be noted that the optimal solution to the objective $$F(a, b) = \Sigma_j w_j (a x_j + b - y_j)^2 \tag{14}$$

is $$a = \frac{\begin{vmatrix} \Sigma_j w_j y_j & \Sigma_j w_j x_j \\ \Sigma_j w_j x_j y_j & \Sigma_j w_j x_j^2 \end{vmatrix}}{\begin{vmatrix} \Sigma_j w_j & \Sigma_j w_j x_j \\ \Sigma_j w_j x_j & \Sigma_j w_j x_j^2 \end{vmatrix}} \tag{15}$$

and $$b = \frac{\begin{vmatrix} \Sigma_j w_j & \Sigma_j w_j y_j \\ \Sigma_j w_j x_j & \Sigma_j w_j x_j y_j \end{vmatrix}}{\begin{vmatrix} \Sigma_j w_j & \Sigma_j w_j x_j \\ \Sigma_j w_j x_j & \Sigma_j w_j x_j^2 \end{vmatrix}} \tag{16}$$

The example optimization proceeds by updating each factor (e.g., D and F) in sequence using Equation (13), and then updating $\rho_s$ and $\rho_d$, which become a and b in Equations (15) and (16). Several iterations of this procedure may be involved before convergence is achieved.

As an example, a user may wish to update the vector representing the factor D. The other factors, as well as $\rho_d$ and $\rho_s$ are held constant. A component of this vector $D_k$ is indexed by k, corresponding to a value of its argument $(\theta_h)_k$. For example, the parametric locations of all BRDF samples being fit whose parametric coordinate $\theta_h$ maps closest to $(\theta_h)_k$ may be indexed by $(\theta_d, \phi_d, \theta_i, \theta_o)_{kj}$. To update $D_k$, the least-squares best solution to the weighted system of equations $$\tilde{p}_{kj} = \rho_d + \rho_s \frac{D_k [F(\theta_d)]_{kj} [G(\theta_i)]_{kj} [G(\theta_o)]_{kj}}{[\cos\theta_i \cos\theta_o]_{kj}} \tag{17}$$

may be determined, wherein the weight corresponding to equation j above is $w_j$. An optimal solution is given by Equation (13) with $$x = D_k \tag{18}$$

$$z_j = \tilde{p}_{kj} - \rho_d$$

$$y_j = \rho_s \frac{[F(\theta_d)]_{kj} [G(\theta_i)]_{kj} [G(\theta_o)]_{kj}}{[\cos\theta_i \cos\theta_o]_{kj}}$$

The geometric factor G may either be treated as an independent tabulated factor, or may be derived from D using a shadowing formula from the microfacet theory. If G is determined from D, then a nonlinear dependence is introduced into the relaxation and it becomes uncertain whether the resulting factor is optimal. In accordance with example techniques discussed herein, this problem may be solved by computing D using the AWLS step, deriving G from this D, and then checking to determine whether the objective function has decreased. If not, a simple 1D minimization (e.g., a golden section search) may be introduced that may reduce the objective along the line from the previous state of the vector D to the new one computed from the AWLS step.

As discussed further below, experimental results have shown advantageously accurate. Such advantageous fitting may be the result of use of a more general model for each of the factors, and advantageously weighted fitting to the entire 3D measurement.

Figure 2A:
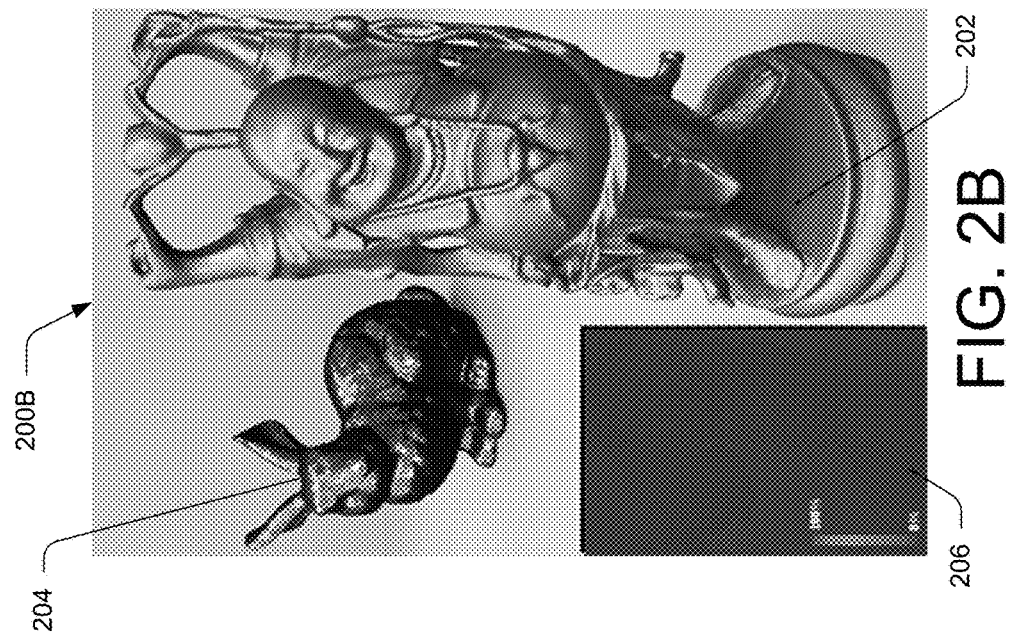
FIGS. 2A-2B illustrate an example measurement and an example rendering using an example BRDF fit.
Figure 2B:
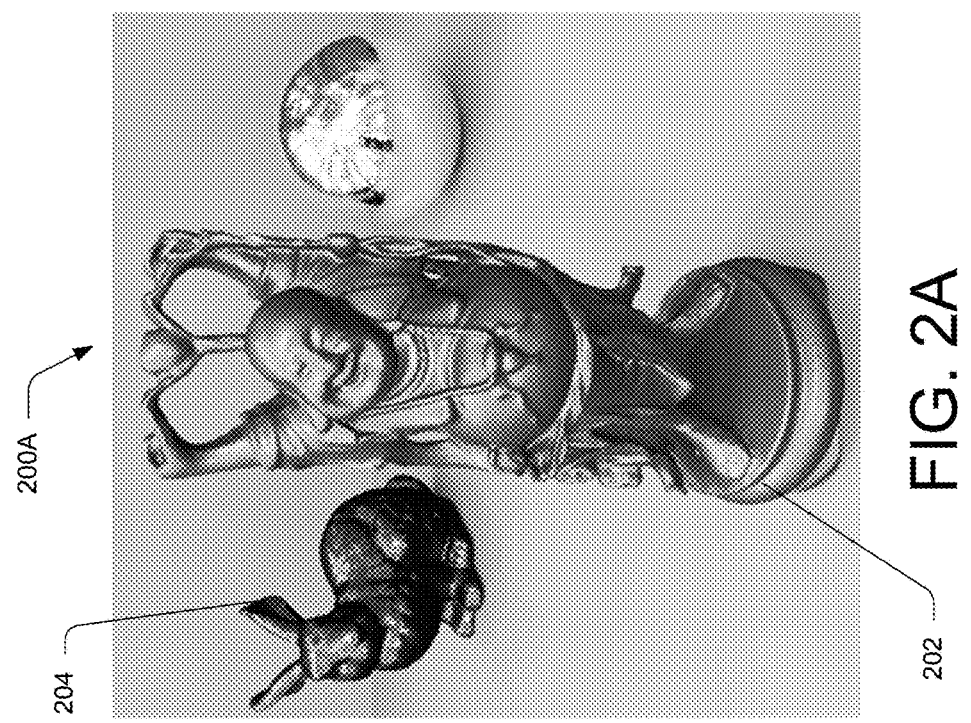

FIGS. 2A-2B illustrate an example measurement 200A and an example rendering 200B using an example nonparametric BRDF fit as discussed herein. As shown in FIG. 2A, a Buddha geometry 202 uses a gold metallic paint material (color not shown as gold), a bunny 204 is chrome-steel, and floors and wall are white-paint from the MERL database. A false-color error visualization 206 is shown in the inset of FIG. 2B.

One skilled in the art of data processing will appreciate that many other types of techniques may be used for the representation for the reflectance of isotropic materials, without departing from the spirit of the discussion herein.

II. Example Operating Environment

Features discussed herein are provided as example embodiments that may be implemented in many different ways that may be understood by one of skill in the art of data processing, without departing from the spirit of the discussion herein. Such features are to be construed only as example embodiment features, and are not intended to be construed as limiting to only those detailed descriptions.

Figure 3:
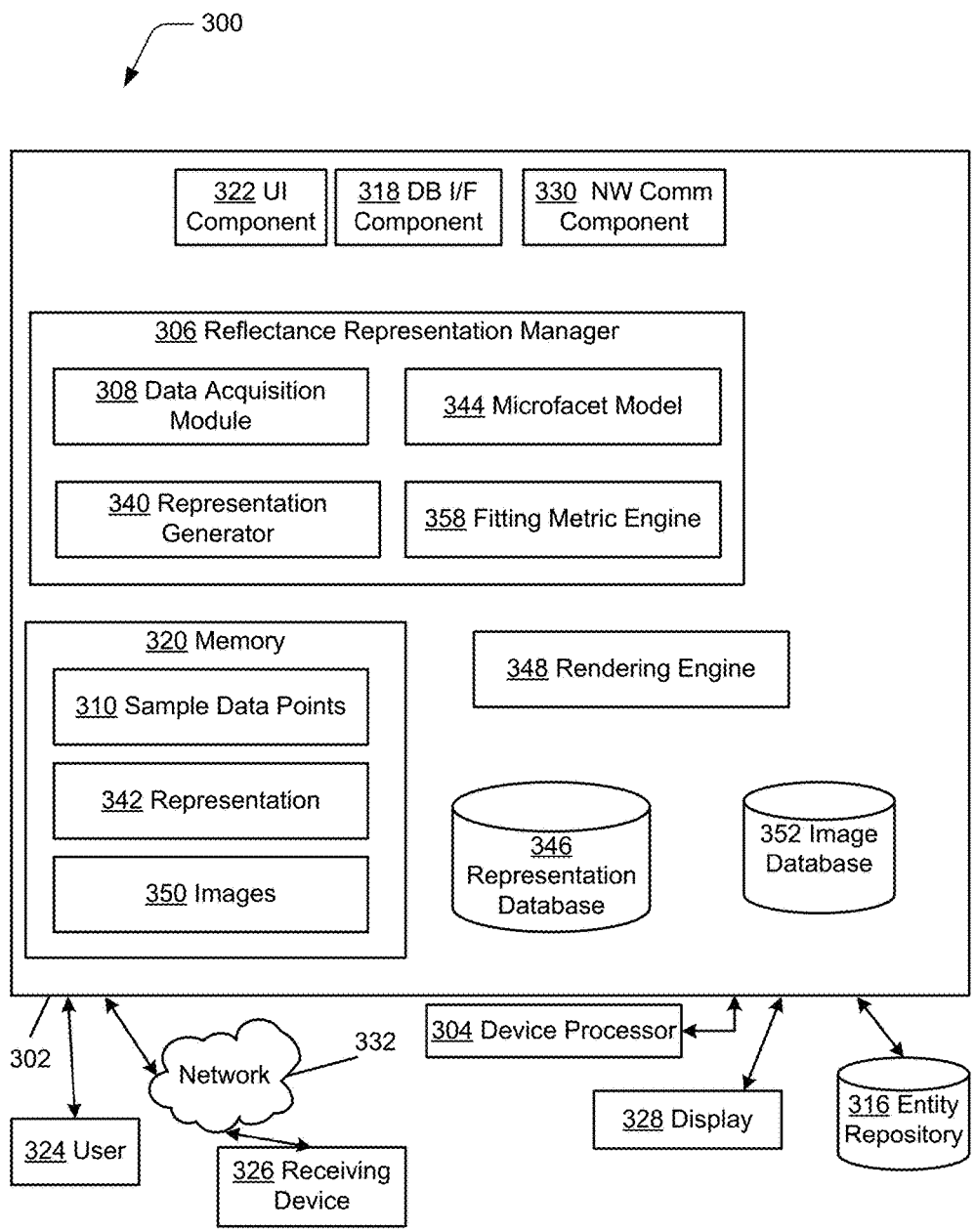
FIG. 3 is a block diagram illustrating an example generalized system for reflectance representation and image rendering.

As further discussed herein, FIG. 3 is a block diagram of a generalized system 300 for representing reflectance. The generalized system 300 as shown is merely intended to illustrate various example functionality and/or logic that may be included in example techniques as discussed herein, and is not intended to be limiting in terms of implementations in various hardware and/or software configurations.

For example, the system 300 may include a computer-readable storage medium storing instructions for execution by at least one processor. As shown in FIG. 3, the system 300 may include a device 302 that includes at least one processor 304. The device 302 may include a reflectance representation manager 306 that may include a data acquisition module 308 that may obtain a plurality of measured sample data points 310 associated with reflectance on a surface of a material.

According to an example embodiment, the reflectance representation manager 306, or one or more portions thereof, may include executable instructions that may be stored on a tangible computer-readable storage medium, as discussed below. According to an example embodiment, the computer-readable storage medium may include any number of storage devices, and any number of storage media types, including distributed devices.

In this context, a "processor" may include a single processor or multiple processors configured to process instructions associated with a processing system. A processor may thus include one or more processors processing instructions in parallel and/or in a distributed manner. Although the device processor 304 is depicted as external to the reflectance representation manager 306 in FIG. 3, one skilled in the art of data processing will appreciate that the device processor 304 may be implemented as a single component, and/or as distributed units which may be located internally or externally to the reflectance representation manager 306, and/or any of its elements.

For example, the system 300 may include one or more processors 304. For example, the system 300 may include at least one tangible computer-readable storage medium storing instructions executable by the one or more processors 304, the executable instructions configured to cause at least one computing apparatus (e.g., a data processing apparatus) to perform operations associated with various example components included in the system 300, as discussed herein. For example, the one or more processors 304 may be included in the at least one computing apparatus. For example, the executable instructions may be implemented as logic (e.g., programmed logic, logic circuitry, etc.) that is configured for execution by one or more processors. One skilled in the art of data processing will understand that there are many configurations of processors and computing apparatuses that may be configured in accordance with the discussion herein, without departing from the spirit of such discussion. As discussed further below, a "computer-readable storage medium" herein does not refer to, and specifically excludes, a signal per se.

In this context, a "component" may refer to executable instructions or hardware that may be configured to perform certain operations, with hardware assistance. Such instructions may be included within component groups of instructions, or may be distributed over more than one group. For example, some instructions associated with operations of a first component may be included in a group of instructions associated with operations of a second component (or more components). For example, a "component" herein may refer to a type of computational entity configured with functionality that may be implemented by executable instructions that may be located in a single entity, or may be spread or distributed over multiple entities, and may overlap with instructions and/or hardware associated with other components. In this context, "executable" instructions refer to instructions that are specifically configured for execution by one or more hardware devices, and do not refer to software per se.

According to an example embodiment, the reflectance representation manager 306 may be implemented in association with one or more user devices. For example, the reflectance representation manager 306 may communicate with one or more servers, as discussed further below.

For example, an entity repository 316 may include one or more databases, and may be accessed via a database interface component 318. One skilled in the art of data processing will appreciate that there are many techniques for storing repository information discussed herein, such as various types of database configurations (e.g., relational databases, hierarchical databases, distributed databases) and non-database configurations.

According to an example embodiment, the reflectance representation manager 306 may include a memory 320 that may, for example, store intermediate data for the reflectance representation manager 306. In this context, a "memory" may include a single memory device or multiple memory devices configured to store data and/or instructions. Further, the memory 320 may span multiple distributed storage devices.

According to an example embodiment, a user interface component 322 may manage communications between a user 324 and the reflectance representation manager 306. The user 324 may be associated with a receiving device 326 that may be associated with a display 328 and other input/output devices. For example, the display 328 may be configured to communicate with the receiving device 326, via internal device bus communications, or via at least one network connection.

According to example embodiments, the display 328 may be implemented as a flat screen display, a print form of display, a two-dimensional display, a three-dimensional display, a static display, a moving display, sensory displays such as tactile output, audio output, and any other form of output for communicating with a user (e.g., the user 324).

According to an example embodiment, the reflectance representation manager 306 may include a network communication component 330 that may manage network communication between the reflectance representation manager 306 and other entities that may communicate with the reflectance representation manager 306 via at least one network 332. For example, the network 332 may include at least one of the Internet, at least one wireless network, or at least one wired network. For example, the network 332 may include a cellular network, a radio network, or any type of network that may support transmission of data for the reflectance representation manager 306. For example, the network communication component 330 may manage network communications between the reflectance representation manager 306 and the receiving device 326. For example, the network communication component 330 may manage network communication between the user interface component 322 and the receiving device 326.

A representation generator 340 may generate a non-parametric densely tabulated one-dimensional representation 342 for a plurality of factors in a microfacet model 344, using the obtained sample data points 310. For example, the representation generator 340 may store the representation 342 in the memory 320 and/or in a representation database 346, which may be included in the system 300, or may be external to the system 300.

In this context, a "microfacet" may refer to a very small (i.e., tiny) facet of the surface of an object being rendered (e.g., used in approximating reflections). For example, a facet may include a flat surface (or substantially flat surface).

In this context, "densely tabulated" may refer to tabulating over a substantially large number of samples, proportional to the sampling density in the parametric coordinates of the original set of measurements being fit. For example, the non-parametric densely tabulated one-dimensional representation may be generated based on 90 samples in the D, F, and G factors, when fit to angular measurements with 90 samples in $\theta_h$ and $\theta_d$, and 180 samples in $\phi_d$.

For example, a rendering engine 348 may render one or more images 350 using the non-parametric densely tabulated one-dimensional representation 342. For example, the rendering engine 348 may store the rendered image 350 in the memory 320 and/or in an image database 352, which may be included in the system 300, or may be external to the system 300.

For example, obtaining the plurality of measured sample data points 310 may include obtaining the plurality of measured sample data points representing measurements of an appearance of brightness of points on the surface.

For example, obtaining the plurality of measured sample data points 310 may include obtaining the plurality of measured sample data points representing measurements of an appearance of brightness of points on the surface, based on the brightness perceived under a plurality of different views and light positions.

For example, the representation generator 340 may generate the non-parametric densely tabulated one-dimensional representation 342 using a fitting metric that is calculated using a sum-of-squares weighting. The weighting includes a non-constant function of measurement magnitudes of the obtained plurality of measured sample data points.

For example, the fitting metric may be minimized using an alternating weighted least squares (AWLS) numerical technique.

For example, the representation generator 340 may generate the non-parametric densely tabulated one-dimensional representation 342 using three one-dimensional functions that are factors in the microfacet model 344, using the obtained sample data points 310.

For example, the factors include a Fresnel factor (F) that represents a dependence of the reflectance on a angle $\theta_d$, a normal distribution function (D) that is a probability distribution function representing a probability that a microfacet normal makes an angle of $\theta_h$ with a surface macro-scale normal, and a geometric factor (G) that represents a microgeometry shadowing and inter-reflecting light onto the micro-geometry itself, as a function of one or more of an obliquity of a light direction or an obliquity of a view direction.

For example, the representation generator 340 may generate the non-parametric densely tabulated one-dimensional representation 342 by applying the microfacet model 344 independently for each color channel of a measurement spectrum.

For example, the representation generator 340 may generate the non-parametric densely tabulated one-dimensional representation 342 by applying the microfacet model 344 independently as a three-channel measurement each of a red channel, a green channel, and a blue channel, for an RGB (red-green-blue) measurement spectrum.

In another aspect, the data acquisition module 308 may obtain a plurality of measured sample data points 310 associated with reflectance on a surface of a material. A fitting metric engine 358 may fit the obtained sample data points 310 to a model by applying a model fitting metric to the obtained sample data points 310, the model fitting metric calculated using a nonnegative, nonzero power of a ratio of a first function and a second function, the first and second functions defined over normalized values of the plurality of measured sample data points 310, the first function defined as a compressive function, the second function defined as a non-asymptotically increasing function (i.e., a function that is increasing in a manner that is not asymptotic). For example, the first and second functions may be defined as discussed with regard to Equations (29) and (30) below. As shown in the examples of Equations (29) and (30), the compressive numerator levels off, while the denominator may continue to increase without limit.

For example, "asymptotic" may refer to approaching a given value as an expression containing a variable tends to a limit (e.g., infinity).

For example, the obtained measured sample data points 310 includes a plurality of measured sample data points 310 representing reflectance on a surface of a material.

For example, the model fitting metric may include a volume form weighting based on a three-angle parameterization.

For example, the model fitting metric may include a bidirectional reflectance distribution function (BRDF) importance weighting based on a BRDF in a local shading integral over incident lighting directions.

For example, the model fitting metric may be minimized using an alternating weighted least squares (AWLS) numerical technique.

For example, the measured sample data points may include a measured sample of high dynamic range (HDR) data points that include a set of data points having values greater than a predetermined threshold.

In another aspect, the data acquisition module 308 may obtain a plurality of measured sample data points associated with reflectance on a surface of a material.

The fitting metric engine 358 may fit the plurality of measured sample data points 310 to a model by applying a fitting metric to the obtained sample data points 310, the fitting metric calculated using a sum-of-squares weighting, the sum-of-squares weighting including a non-constant function of measurement magnitudes of the obtained plurality of measured sample data points 310.

For example, the sum-of-squares weighting may include squared differences between predictions of the model and actual measurement values.

For example, obtaining the plurality of measured sample data points may include obtaining the plurality of measured sample data points representing measurements of an appearance of brightness of points on the surface.

For example, the fitting metric may be calculated using a plurality of subweights, the subweights including a volume form weighting based on a three-angle parameterization.

For example, the fitting metric may be calculated using a plurality of subweights, the subweights including a bidirectional reflectance distribution function (BRDF) importance weighting based on a BRDF in a local shading integral over incident lighting directions.

For example, the representation generator 340 may generate a non-parametric densely tabulated one-dimensional representation 342 for a plurality of factors in a microfacet model 344, using the obtained sample data points 310.

Example techniques discussed herein may utilize the fitting power of the microfacet model for isotropic BRDFs measured from real materials. The example non-parametric factor model discussed herein may exploit the model's functional structure while advantageously omitting restricted parameterizations for its factors. An example objective function may be based on compressive weighting for measuring fitting error in high dynamic range BRDFs. Example metrics as discussed herein may advantageously improve control of rendering error.

Further, an example numerical procedure (or technique) may be used to minimize the objective function and handle dependencies that arise between factors.

Experimental results have indicated that the microfacet model with general 1D factors provides advantageous representational power and faithfully yet compactly captures a comprehensive set of materials, in contrast with conventional parametric approaches.

Photorealistic image synthesis involves global simulation of light transport in a scene through numerical solution of the rendering or radiative transport equations, as well as local modeling of light's interaction at surfaces or volumetric particles. Local interactions are further classified as reflection, transmission, scattering, or sub-surface events. Regardless of the accuracy of global light transport simulation, synthetic images may appear unrealistic if the local model fails to faithfully capture the behavior of real-world materials.

In accordance with example techniques discussed herein, a restricted space of isotropic local surface reflection, which is invariant to simultaneous rotation of light and view vectors around the surface normal, may be employed. Here, the 4D bi-directional reflectance distribution function (BRDF) that governs reflectance at a particular surface point reduces to a 3D function. This neglects examples with directionally aligned surface micro-geometry like scratches (on brushed metal) or fibers (in hair or fabric), but still includes a wide and interesting class of common materials.

Even in the isotropic case, BRDF representation may be challenging. For example, some conventional representations may rely on large tabulated datasets that may be difficult to edit and costly to store and access in a rendering system, or on compact parametric models that may be incapable of accurately capturing many real materials.

The microfacet theory may advantageously aid in this representational problem, as it models coarse-scale surface reflection as a product of several factors derived from the statistical distribution of micro-scale geometry, as discussed further below. Several realizations have been proposed that define simple analytic models for the various factors in tens of a few parameters. However, these factor models may not capture a broad range of realistic reflectance. However, by separating the theory's functional structure from specific, highly-constrained models used for its factors, the generalized representation is advantageously still compact yet powerful enough to capture real-world reflectance. Such an example representation may be referred to herein as the "non-parametric factor microfacet model."

Example techniques discussed herein may express the fitting of this nonparametric factor model to high dynamic range (HDR) data from measured BRDFs as a standard minimization problem. However, optimization objectives used in conventional work may lead to high error when the resulting fits are used for rendering. Therefore, example techniques discussed herein utilize an example objective that combines compressive weighting (e.g., Equation 29) with weights based on the BRDFs parametric volume form (e.g., Equation 26) and its importance in the local rendering integral (e.g., Equation 28). For example, similar to techniques in robust statistics, example techniques discussed herein may advantageously reduce the importance of error in bright BRDF peaks to better match its darker but broader areas. Further, an example alternating weighted least squares (AWLS) solver may perform the minimization. For example, the AWLS solver may be somewhat similar to approaches in tensor approximation, but handles nonlinear dependencies between factors and factor variables that arise in the microfacet model. Such example techniques may be straightforward to implement, quickly converging, robust to random initialization, and completely automatic with no per-material parameter tweaking involved. Such example techniques may provide fits that are consistently accurate, both quantitatively and visually.

Example models discussed herein may include three tabulated ID vectors, one each for the shadowing-masking G, microfacet distribution D, and Fresnel F factors, as well as the scalar diffuse and specular coefficients $\rho_d$ and $\rho_s$ (e.g., Equation 21). As further discussed herein, this example model may be fitted independently to each color (RGB) channel of the data. For example, at least two alternative formulations of the G factor are discussed herein, one that determines it from D using an example shadowing model, and another that is data-driven. The second method may improve the fit for many of the more diffuse materials, but may increase the fitting cost. Both methods may provide the power of a compact, data-driven model governed by the microfacet's non-orthogonal but physically motivated factorization.

BRDF reflectance data may be directly captured with gonioreflectometers. Sampling noise and limited resolution may involve corrective post-processing if the data is to be used for image synthesis. For example, a MERL dataset (see, e.g., Matusik et al., "A data-driven reflectance model," In *ACM SIGGRAPH* 2003 Papers, ACM, pages 759-769) includes a large set (e.g., 100) of isotropic BRDFs captured at high angular resolution (e.g., 1.5 million samples).

Analytic BRDF models (e.g., parametric models) may serve as alternatives to data-driven representations; however, such parametric models may lead to a reduction in accuracy. For example, parametric models may be validated against real-world BRDFs using least-squares fits to the MERL dataset.

In broad terms, the microfacet theory of reflection from rough surfaces states that large-scale reflection behavior is the result of reflections (and interreflections) at a micro-geometric scale. The geometry and material composition of this micro-structure may ultimately control a material's reflectance. A microfacet model imposes a mathematical form on the micro-surface properties. For example, for computer graphics, a statistical distribution of the micro-geometric facet orientations may be leveraged to derive analytic shadowing-masking factors.

Analytic basis representations may be used in realistic and interactive rendering, including the compact representation of BRDFs. For example, spherical harmonics (SH) representations may be compact and provide efficient reconstruction and sampling, but may be limited to "low-frequency" reflectance from diffuse and mildly-glossy BRDFs. For example, wavelets represent a wider-range of reflectance behaviors, with similar efficiency benefit but with larger storage cost. For example, spherical radial basis functions (SRBFs) may be used for interactive rendering to better balance accuracy, reconstruction and sampling efficiency. For example, a rational function representation may be used to fit real-world reflectance. However, such a representation may be unstable and costly to fit.

A tabulated "basis" representation may also be used for BRDF representation. In general terms, if the BRDF of an object is interpreted as a four-dimensional tabulated dataset, tensor approximation techniques may be employed to more compactly factorize and represent the data. For example, techniques from numerical algebra may be applied to factorize BRDF datasets, where different types of factorization and tabulation parameterization may be employed. These approaches may involve many factors to obtain low-error fits to real-world reflectance data.

Example techniques discussed herein may employ the three ID-term factorization implicit in the microfacet model, and may advantageously obtain accurate and compact fits.

As another example, inverse shade trees may enforce an overall functional structure to infer simpler 1D and 2D factors. Such a model is not based on microfacet theory.

Microfacet factors are not all direct functions of the independent variables, so example techniques discussed herein may be interpreted as "non-orthogonal" tensor factorizations. Specifically, non-linear dependencies between factors arise from the shadowing-masking (G) factor's dependence on $\theta_i$ (or $\theta_o$) (e.g., Equations 19 and 20). This factor also appears twice, each time as a function of a different derived angle. Further, one form of an example model discussed herein may explicitly derive the shadowing-masking factor using a double integration of the microfacet distribution factor D.

An example weighted linear regression is discussed below.

While robust techniques for regression analysis may be ubiquitous in statistics and experimental analysis, computer graphics (CG) reflectance modeling may involve heteroscedasticity (see, e.g., White, H., "A heteroskedasticity-consistent covariance matric estimator and a direct test for heteroskedasticity," *Econometrica* 48, 4, (1980), pages 817-838): statistical variables such as BRDF samples may differ in terms of their variances and expected measurement errors. An example solution may include weighted linear regression, where the weights are inversely proportional to sample variance. For example, the weight may be a direct function (e.g. reciprocal or reciprocal squared) of the dependent variable or measured response, (e.g., least-squares percentage regression). For example, such techniques may be used for compressive weighting as discussed below, augmented by a compressive numerator that ensures that the weighting does not become arbitrarily high as the BRDF measurement approaches 0.

An example microfacet model is discussed below.

In the canonical local coordinate frame, the surface normal may be denoted by n=(0, 0, 1). For example, the light direction may be denoted by i, the view direction by o, and the halfway vector midway between them by $h=(i+o)/\|i+o\|$. These example vectors are 3D unit vectors.

An isotropic BRDF is invariant to rotation of the halfway vector around the normal, and may be parameterized by three angles ($\theta_h$, $\theta_d$, $\theta_d$) derived from n, i, and o. The angle between the halfway vector and normal may be denoted $$\theta_h \in \left[0, \frac{\pi}{2}\right]$$

where $\cos \theta_h = n \cdot h$. The angle $$\theta_d \in \left[0, \frac{\pi}{2}\right]$$

is formed between the view or light direction and the halfway vector: $\cos \theta_d = i \cdot h = o \cdot h$. Further, the angle $\phi_d \in [0, \pi]$ denotes the rotation of the light direction about h, and may be defined by $$\cos\phi_d = i_h^\perp \cdot n_h^\perp$$

where $$u_v^\perp = \frac{u - (u \cdot v)v}{\|u - (u \cdot v)v\|}$$

denotes the perpendicular projection of u onto v.

The angle between the light direction and normal, $\theta_i$, and between the view direction and normal $\theta_o$, may be determined from the three-parametric angles via:

$$\cos \theta_i = \cos \theta_h \cos \theta_d + \cos \theta_h \cos \theta_d \cos \phi_d, \quad (19)$$

$$\cos \theta_o = \cos \theta_h \cos \theta_d - \cos \theta_h \cos \theta_d \cos \phi_d, \quad (20)$$

BRDF samples will lie in the positive hemisphere of n: in other words, $\theta_i, \theta_o \in [0, \pi/2]$. For example, the above formulas may be derived using the parameterization discussed below (e.g., in a discussion of an example derivation of an isotropic BRDF parameterization shown below).

Given this parameterization, the microfacet model represents BRDFs in terms of three ID factor functions via:

$$\rho(\theta_h, \theta_d, \phi_d) = \rho_d + \rho_s\left(\frac{D(\theta_h)F(\theta_d)G(\theta_i)G(\theta_o)}{\cos\theta_i \cos\theta_o}\right) \quad (21)$$

The D factor may be referred to as the normal distribution function (NDF), representing the probability that a microfacet normal makes an angle of $\theta_h$ with the macro-scale normal n. The F factor may be referred to as the Fresnel factor, modeling reflectance variation in the $\theta_d$ parameter. The geometric factor G models shadowing, masking, and inter-reflection effects, in terms of the obliquity of the view or light direction, $\theta_i$ or $\theta_o$. The reciprocity property affirms that $\rho$ is unchanged if i and o are exchanged, thus implying that the same G factor will be shared for both the $\theta_i$ and $\theta_o$ arguments. For conciseness, the notation drops the division by $\pi$ usually present in the definition of the diffuse and specular coefficients, $\rho_d$ and $\rho_s$.

To test the validity of the microfacet model, an example naive model may be defined as:

$$\rho(\theta_h, \theta_d, \phi_d) = \rho_d + \rho_s D(\theta_h) F(\theta d) H(\phi_d) \quad (22)$$

which factorizes directly in terms of the parameterization variables.

For example, a user may fit to the MERL database which stores measurements for 100 different isotropic materials. Each material measurement is stored in a uniformly-sampled 3D block of ($\theta_h$, $\theta_d$, $\phi_d$) parameter space with angular sampling 90×90×180, for each RGB color channel. The $\theta_h$ dimension is further transformed via:

$$\theta_h' = \sqrt{\theta_h}. \quad (23)$$

which provides denser sampling close to 0, in the region of the specular highlight. $\theta_h'$ is sampled uniformly in $[0, \sqrt{\pi/2}]$.

The example model in Equation (21) may be applied to fit each color channel measurement separately. For each color channel, a user may solve for three vectors each including 90 components (representing sampled factor functions D, F, and G), and two scalars ($\rho_d$ and $\rho_s$).

Example techniques for fitting non-parametric microfacet factors are discussed below.

In discussion of an example fitting objective (e.g. in discussion of a "fitting metric"), the following sum may be minimized over all measured BRDF samples indexed by j:

$$F = \Sigma_j w_j (\rho(\theta_h, \theta_d, \phi_d)_j - \rho^*_j)^2 \quad (24)$$

wherein $\rho^*_j$ is the measured BRDF sample, ($\theta_h$, $\theta_d$, $\phi_d$)$_j$ represents its parametric coordinates, and $\rho$ is evaluated from Equation (21). The weight $w_j$ may be provided by the product of three subweights via $$w_j = w_T(\theta_h, \theta_d, \phi_d)_j w_I(\theta_h, \theta_d, \phi_d)_j w_C(\rho^*_j). \quad (25)$$

The three example subweights are discussed further below. It may be noted that global constants in these definitions may not affect the minimization, and may be ignored.

Volume form weighting is discussed below.

The first subweight arises from the three-angle parameterization of isotropic BRDFs, and maybe denoted as:

$$w_V = \sqrt{8\sin^2\theta_d(\cos^2\theta_d + \sin^2\theta_d\cos^2\phi_d)d\theta_h d\theta_d d\phi_d}. \qquad (26)$$

An example weighting as discussed herein may be determined by the volume form of the mapping between the $(\theta_h, \theta_d, \phi_d)$ parameter space and the (i, o) output space of pairs of unit directions. An example derivation of this formula is discussed below in an example derivation of a parametric weighting for an isotropic BRDF. Since the BRDF parameterization is in terms of $\theta'_h$ rather than $\theta_h$, Equation (23) implies that $$d\theta_h = 2\theta'_h d\theta'_h = 2\sqrt{\theta_h} d\theta'_h. \qquad (27)$$

BRDF importance weighting is discussed below.

The second subweight may be denoted as:

$$w_I = \cos\theta_i \cos\theta_o. \qquad (28)$$

The $\cos\theta_i$ factor arises because it multiplies the BRDF in the local shading integral over incident lighting directions. The $\cos\theta_o$ factor is included for reciprocal symmetry and because surface points are more likely to appear as their normal aligns with the view direction.

An example compressive weighting technique is discussed below.

The final subweight may arise because more measurement error may be expected in a higher-magnitude BRDF sample. For example, a user may decide to not try as hard to fit high values $\rho^*_j$ as low ones. This subweight may be denoted as:

$$w_C = \left(\frac{f(\rho^*_j/\bar{\rho})}{\rho^*_j/\bar{\rho}}\right)^p \qquad (29)$$

where f is a compressive function of the form $$f(x;\alpha) = \frac{1}{\alpha}(1 - e^{-\alpha x}) \qquad (30)$$

and $\bar{\rho}$ is the weighted median of the BRDF with weight given by the product $w_V w_I$. The weighting power p is a parameter that may, for example, be selected in the range [1, 2]. The bigger the value of p, the higher the weight value that may be assigned to darker parts of the BRDF relative to its bright parts. For example, the value p=1.4 may be fixed for fits.

Figure 4:
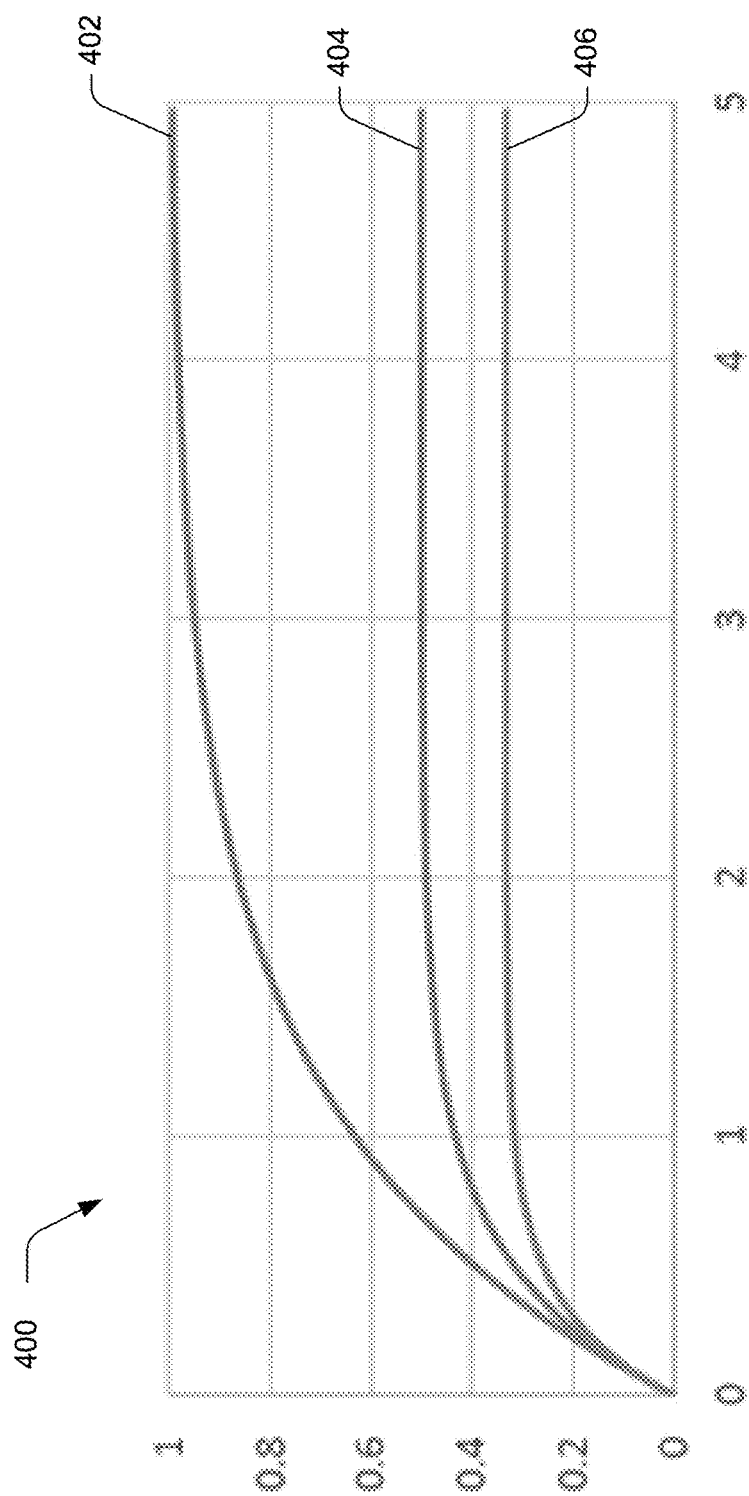
FIG. 4 is a graphical illustration of an example compressive function.

FIG. 4 is a graphical illustration 400 of an example compressive function, in accordance with example techniques discussed herein. The compressive function in Equation (30) maps all non-negative real numbers x to the finite interval $[0, 1/\alpha]$. The bigger the value of $\alpha$, the more compressive the transformation becomes; i.e., the more high values are squeezed close to the function's asymptote of $1/\alpha$. For example, as shown in FIG. 4, a curve 402 illustrates $f(x; \alpha)$ for $\alpha=1$, a curve 404 illustrates $f(x; \alpha)$ for $\alpha=2$, and a curve 406 illustrates $f(x; \alpha)$ for $\alpha=3$. the In accordance with example techniques discussed herein, a value of $\alpha = \log 2$ may be fixed in order to map the BRDF weighted median to the center of the output range (i.e., to $\frac{1}{2}\alpha$).

It may be noted that $\lim_{x \to 0} f(x)/x = 1$. The maximum value of $w_c$ is therefore 1. From this maximum at $x = \rho^*_j/\bar{\rho} = 0$, it decreases monotonically to 0 as the BRDF value $\rho^*_j \to \infty$. There is no difficulty with weights becoming arbitrarily large as $\rho^*_j \to 0$ as is the case with an example simpler alternative of weighting by the measurement reciprocal $w_c = (\rho^*_j)^{-p}$. Away from 0, this compressive weighting scheme is substantially similar to the simpler scheme.

An example fitting technique is discussed below.

AWLS is an iterative procedure that repeatedly updates each factor in sequence until the process converges. To update a single factor, everything else may be held constant, and the procedure may then solve for the single factor's optimal weighted least-squares value, so that the iteration proceeds "downhill" in the objective. Each factor involves multiple components representing a 1D sampled function. As illustration of how each factor component may be computed, an example simplified objective may be denoted as:

$$F(x) = \Sigma_j w_j(z_j - xy_j)^2. \qquad (31)$$

wherein x represents an individual factor component to be solved for. The minimizing solution may be denoted as:

$$x = \frac{\sum_j w_j y_j z_j}{\sum_j w_j y_j^2}. \qquad (32)$$

At each factor component "bin," the weighted sums representing the above numerator and denominator may be accumulated over all BRDF samples that map there. The optimal value of the component may then be provided by the division in Equation (32).

To solve for $\rho_d$ and $\rho_s$, it may be noted that the optimal solution to the simplified objective:

$$F(a,b) = \Sigma_j w_j(ax_j + b - y_j)^2 \qquad (33)$$

may be computed by Cramer's rule:

$$a = \left\|\begin{array}{cc} \sum_j w_j y_j & \sum_j w_j x_j \\ \sum_j w_j x_j y_j & \sum_j w_j x_j^2 \end{array}\right\| \bigg/ \left\|\begin{array}{cc} \sum_j w_j & \sum_j w_j x_j \\ \sum_j w_j x_j & \sum_j w_j x_j^2 \end{array}\right\| \qquad (34)$$

$$b = \left\|\begin{array}{cc} \sum_j w_j & \sum_j w_j y_j \\ \sum_j w_j x_j & \sum_j w_j x_j y_j \end{array}\right\| \bigg/ \left\|\begin{array}{cc} \sum_j w_j & \sum_j w_j x_j \\ \sum_j w_j x_j & \sum_j w_j x_j^2 \end{array}\right\| \qquad (35)$$

If the optimal b<0, it may be clamped to 0 and the following (simpler) formula may be applied to determine an optimal $\alpha$ via:

$$\alpha = \frac{\sum_j w_j x_j y_j}{\sum_j w_j x_j^2}. \qquad (36)$$

The optimization may proceed by updating each factor component (e.g., D or F) using Equation (32), and may then update $\rho_s$ and $\rho_d$ which become a and b in Equations (34) and (35).

More specifically, a user may wish to update the factor D. The other factors as well as $\rho_d$ and $\rho_s$ may be held constant. For example, assuming that a component of D is indexed by k, corresponding to a particular value of its argument $(\theta_h)_k$, and assuming that the parametric locations of all BRDF samples whose $\theta_h$ coordinate maps to $(\theta_h)_k$ are indexed by $(\theta_d, \phi_d, \theta_i, \theta_o)_{kj}$, then to update $D_k$, the least-squares best solution to the weighted system of equations indexed by j may be determined as:

$$\rho^*_{kj} = \rho_d + \rho_s \frac{D_k [F(\theta_d)]_{kj}[G(\theta_i)]_{kj}[G(\theta_o)]_{kj}}{[\cos\theta_i \cos\theta_o]_{kj}}, \quad (37)$$

where, as before, equation j is weighted by $w_j$. An example optimal solution is given by (13) with $$x = D_k, \quad (38)$$
$$z_j = \rho^*_{kj} - \rho_d,$$
$$y_j = \rho_s \frac{[F(\theta_d)]_{kj}[G(\theta_i)]_{kj}[G(\theta_o)]_{kj}}{[\cos\theta_i \cos\theta_o]_{kj}}.$$

The F factor may be updated similarly, as well as the H factor in the naive model.

G may either be treated as an independent tabulated factor, or may be derived from D using a shadowing model. When evaluating G or the cosine factors in Equation (21), linear interpolation may be applied in the $\theta_i$ or $\theta_o$ space. This may be avoided for D and F since all BRDF samples $\rho^*_j$ are uniformly parameterized in $\theta'_h$ and $\theta_d$, and map onto the corresponding vector component.

Determining G from D introduces a nonlinear dependence in the relaxation, so that the solved-for D is no longer optimal. This issue may be addressed by computing D using the example AWLS step, deriving G from it, and then explicitly checking whether the objective function has decreased. If not, a simple 1D minimization may be applied based on a golden section search (GSS) that reduces the objective along the line from D's previous state to its new one.

G can be computed from D via a double integration:

$$G(\theta) = (1 + \Lambda(\cot\theta))^{-1} \quad (39)$$

$$\Lambda(\mu) = \frac{1}{\mu} \int_{\tan^{-1}\mu}^{\frac{\pi}{2}} (\tan\omega - \mu)(1 = \tan^2\omega) p_2(\tan\omega) d\omega \quad (40)$$

$$p_2(r) = 2 \int_0^{\frac{\pi}{2}} p_{22}(r^2 + \tan^2\psi)(\tan^2\psi + 1) \, d\psi \quad (41)$$

$$p_{22}(u) = D(\tan^{-1}\sqrt{u})\cos^4(\tan^{-1}\sqrt{u}) \quad (42)$$

These formulas may be derived using variables $\psi = \tan^{-1} q$, $\omega = \tan^{-1} r$, and $u = \tan^2 \theta_h$. To numerically evaluate the above integrals, accuracy may be obtained using Gaussian quadrature with 15 points. The tabulated D function may be evaluated using linear interpolation.

Solving for G explicitly also introduces a non-trivial dependency. Unlike the other two factors, it appears twice in the microfacet model. In accordance with example techniques discussed herein, a simple heuristic may be applied to solve for it. For example, if the two factors are denoted $G_i = G(\theta_i)$ and $G_o = G(\theta_o)$, then an example AWLS update step may be used to solve for each separately, holding the other (as well as the D and F factors and $\rho_s$ and $\rho_d$ scalars) constant. These two results may then be averaged, and a simple Gaussian smoothing filter may be applied. This procedure may be iterated until it converges. It may then be determined whether the objective increases, and if so, a GSS update may be applied, as in the G-from-D case.

For an example independent-G solution, it may be noted that the cosine factors in (3) are superfluous in the sense that they can be absorbed into the general G factor. In accordance with example techniques discussed herein, they may be retained so that the G factors are comparable between the two methods.

To ensure a physically-plausible dynamic range, each factor component may be clamped to the interval $[\in, 1]$, where $\in = 1e-6$. For example, such DR clamping may be used in independent-G fitting which involves the product of four factors solved for independently ($\rho_s$, D, F, G). Without DR clamping, a user may experience substantially large values for $\rho_s$ and inflated importance of tiny variations in near-zero factor components.

One skilled in the art of data processing will appreciate that many different techniques may be used for volume form weighting, without departing from the spirit of the discussion herein.

III. Flowchart Description

Features discussed herein are provided as example embodiments that may be implemented in many different ways that may be understood by one of skill in the art of data processing, without departing from the spirit of the discussion herein. Such features are to be construed only as example embodiment features, and are not intended to be construed as limiting to only those detailed descriptions.

Figure 5A:
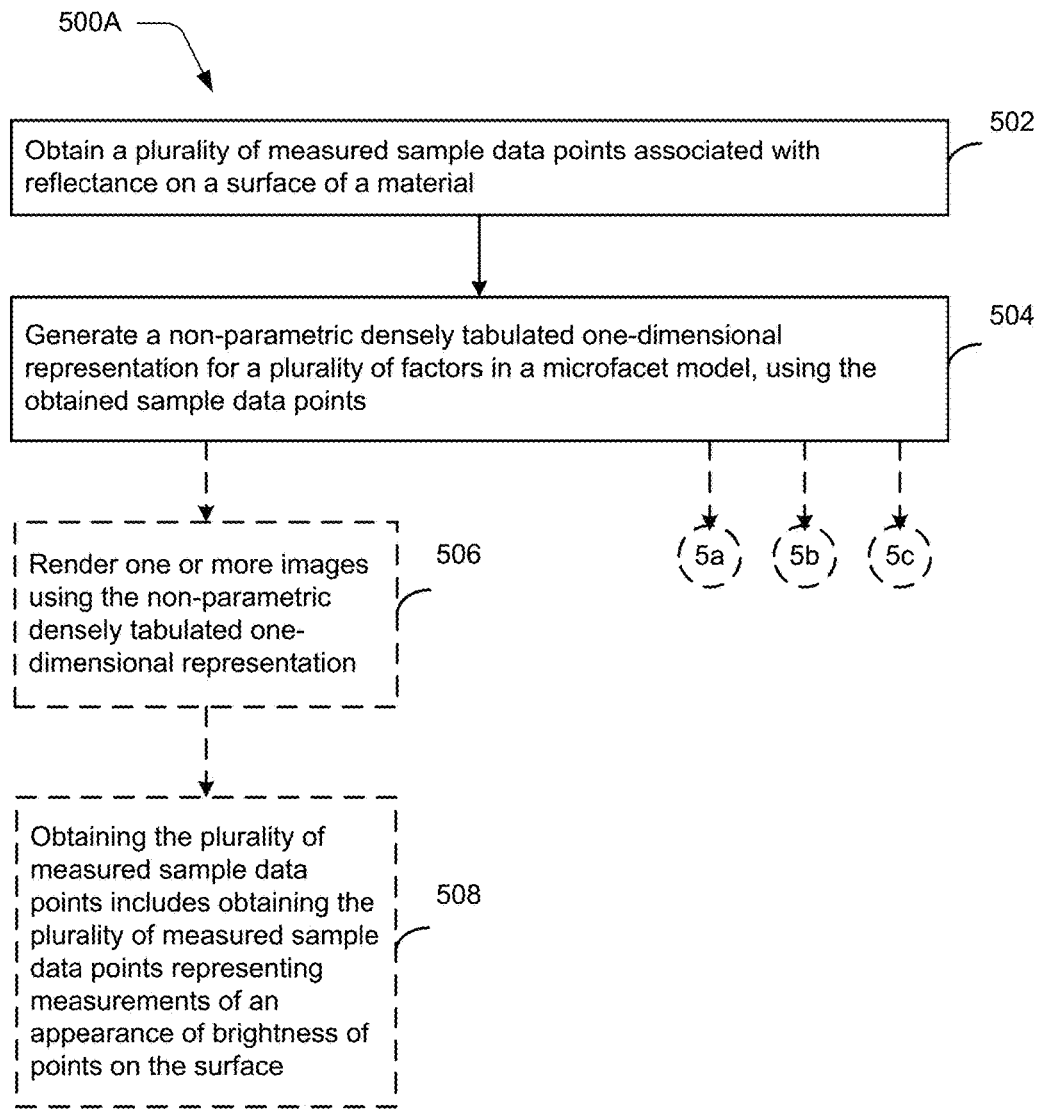
FIGS. 5A-5C are a flowchart illustrating example operations of the system of FIG. 3.
Figure 5B:
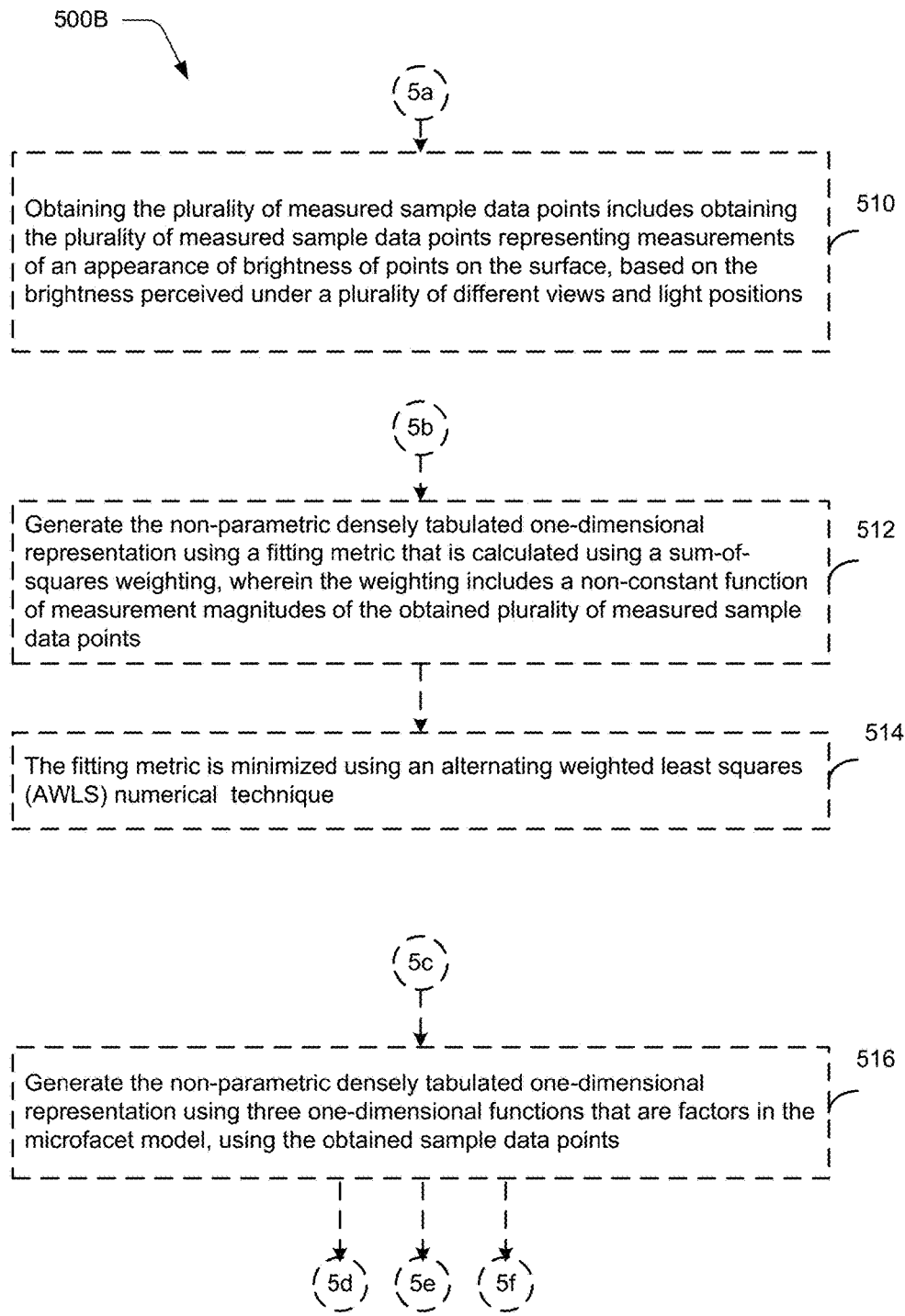
Figure 5C:
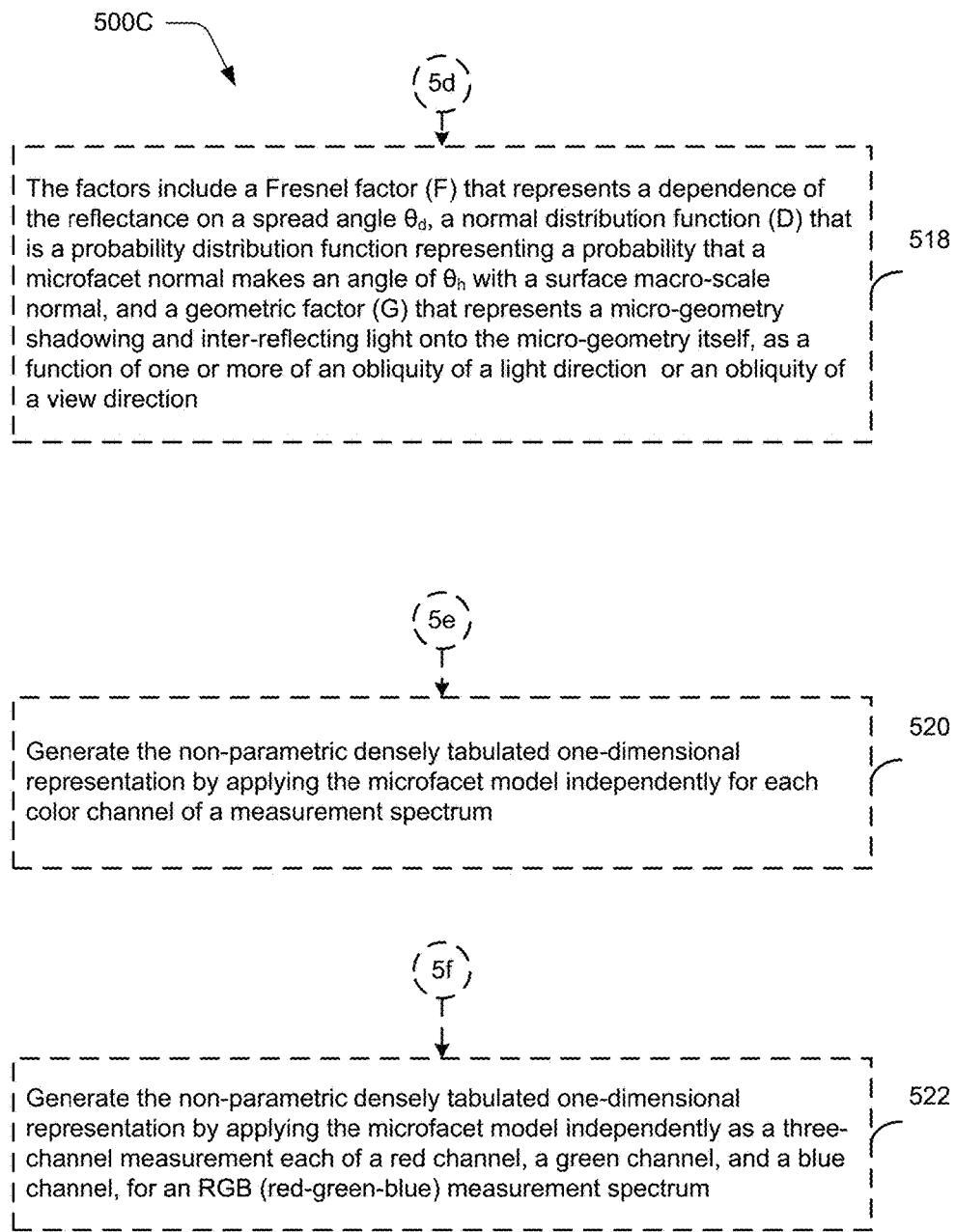

FIGS. 5A-5C are a flowchart illustrating example operations of the system of FIG. 3, according to example embodiments. In the example of FIG. 5A, a plurality of measured sample data points associated with reflectance on a surface of a material may be obtained (502).

A non-parametric densely tabulated one-dimensional representation for a plurality of factors in a microfacet model may be generated, using the obtained sample data points (504).

For example, one or more images may be rendered using the non-parametric densely tabulated one-dimensional representation (506).

For example, obtaining the plurality of measured sample data points may include obtaining the plurality of measured sample data points representing measurements of an appearance of brightness of points on the surface (508).

For example, obtaining the plurality of measured sample data points may include obtaining the plurality of measured sample data points representing measurements of an appearance of brightness of points on the surface, based on the brightness perceived under a plurality of different views and light positions (510), in the example of FIG. 5B.

For example, the non-parametric densely tabulated one-dimensional representation may be generated using a fitting metric that is calculated using a sum-of-squares weighting, wherein the weighting includes a non-constant function of measurement magnitudes of the obtained plurality of measured sample data points (512).

For example, the fitting metric may be minimized using an alternating weighted least squares (AWLS) numerical technique (514).

For example, the representation generator may generate the non-parametric densely tabulated one-dimensional representation using three one-dimensional functions that are factors in the microfacet model, using the obtained sample data points (516).

For example, the factors include a Fresnel factor (F) that represents a dependence of the reflectance on a spread angle $\theta_d$, a normal distribution function (D) that is a probability distribution function representing a probability that a microfacet normal makes an angle of $\theta_h$ with a surface macroscale normal, and a geometric factor (G) that represents a micro-geometry shadowing and inter-reflecting light onto the micro-geometry itself, as a function of one or more of an obliquity of a light direction or an obliquity of a view direction (518), in the example of FIG. 5C.

For example, the non-parametric densely tabulated one-dimensional representation may be generated by applying the microfacet model independently for each color channel of a measurement spectrum (520).

For example, the non-parametric densely tabulated one-dimensional representation may be generated by applying the microfacet model independently as a three-channel measurement each of a red channel, a green channel, and a blue channel, for an RGB (red-green-blue) measurement spectrum (522).

Figure 6A:
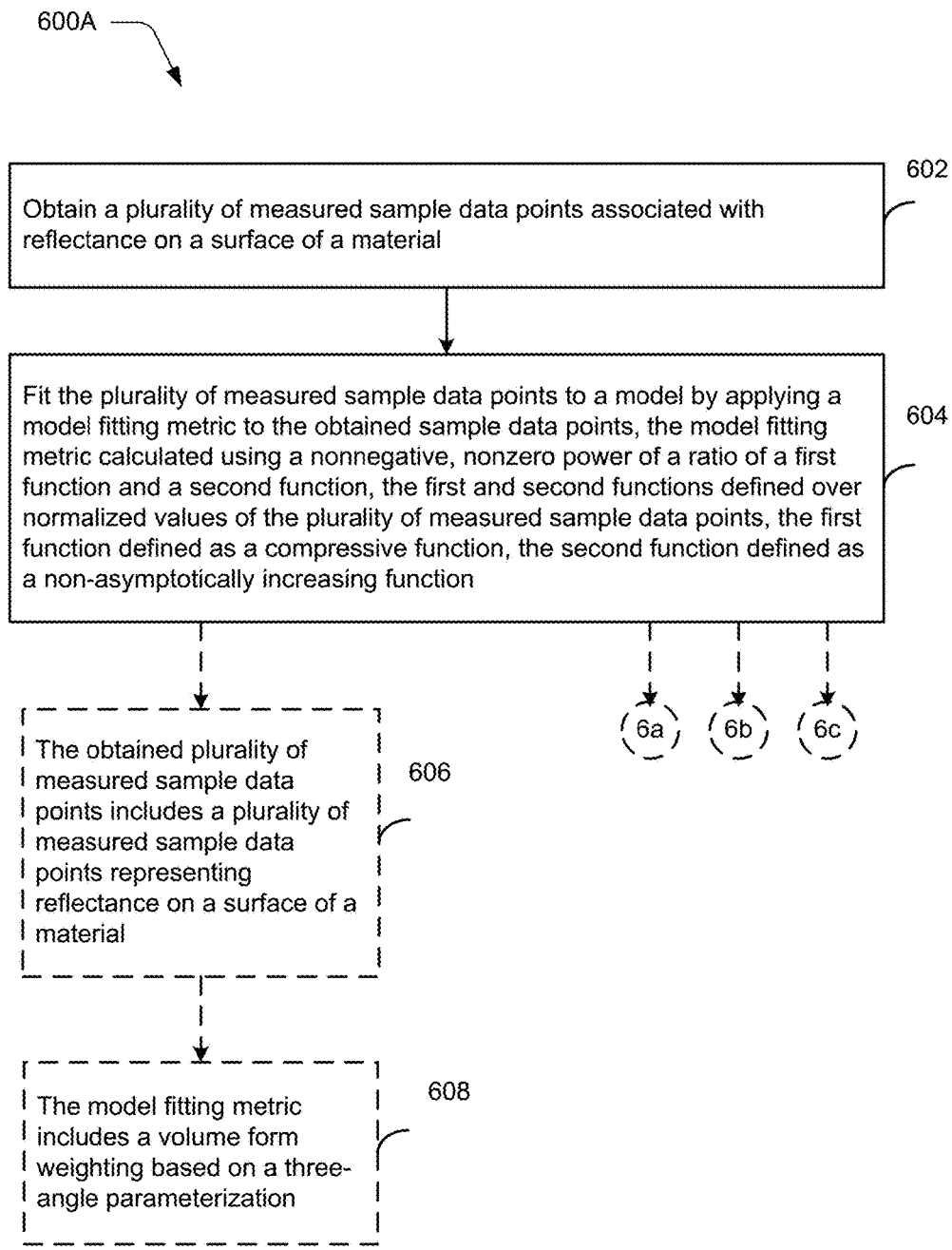
FIGS. 6A-6B are a flowchart illustrating example operations of the system of FIG. 3.
Figure 6B:
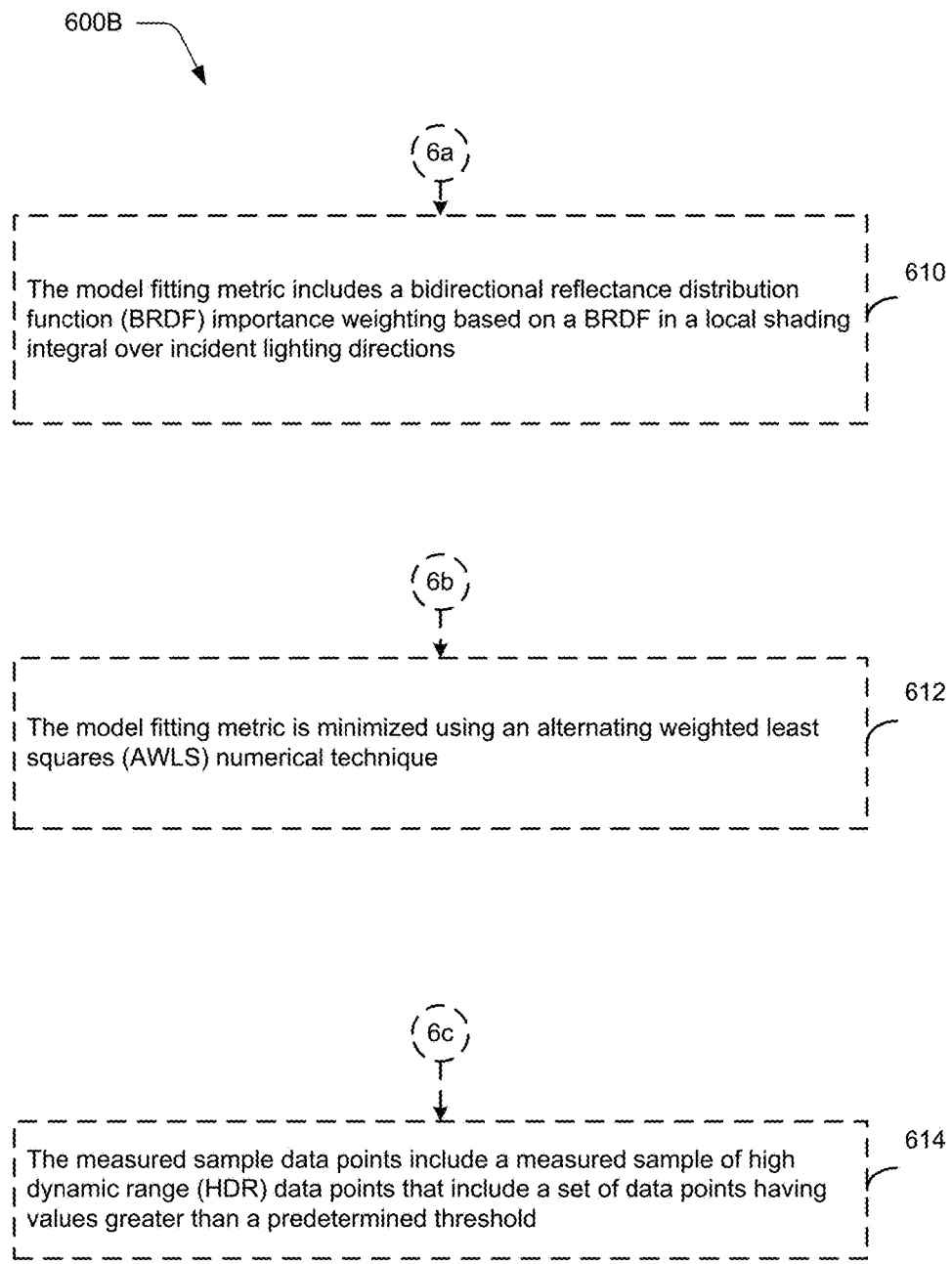

FIGS. 6A-6B are a flowchart illustrating example operations of the system of FIG. 3, according to example embodiments. In the example of FIG. 6A, a plurality of measured sample data points associated with reflectance on a surface of a material may be obtained (602).

The measured sample data points may be fitted to a model by applying a model fitting metric to the obtained sample data points, the model fitting metric calculated using a nonnegative, nonzero power of a ratio of a first function and a second function, the first and second functions defined over normalized values of the plurality of measured sample data points, the first function defined as a compressive function, the second function defined as a non-asymptotically increasing function (604).

For example, the obtained measured sample data points may include a plurality of measured sample data points representing reflectance on a surface of a material (606).

For example, the model fitting metric may include a volume form weighting based on a three-angle parameterization (608).

For example, the model fitting metric may include a bidirectional reflectance distribution function (BRDF) importance weighting based on a BRDF in a local shading integral over incident lighting directions (610), in the example of FIG. 6B.

For example, the model fitting metric may be minimized using an alternating weighted least squares (AWLS) numerical technique (612).

For example, the measured sample data points may include a measured sample of high dynamic range (HDR) data points that include a set of data points having values greater than a predetermined threshold (614).

Figure 7A:
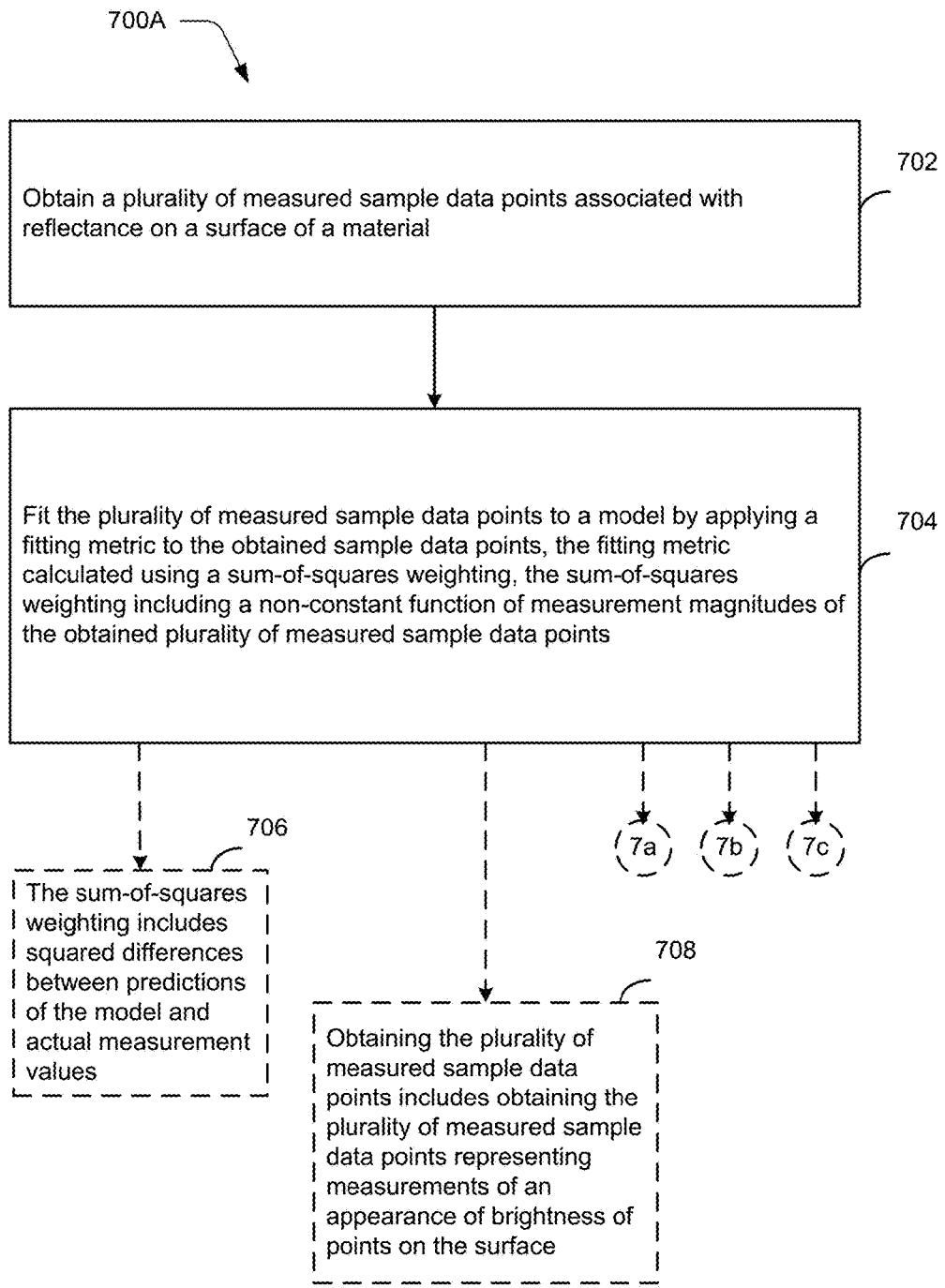
FIGS. 7A-7B are a flowchart illustrating example operations of the system of FIG. 3.
Figure 7B:
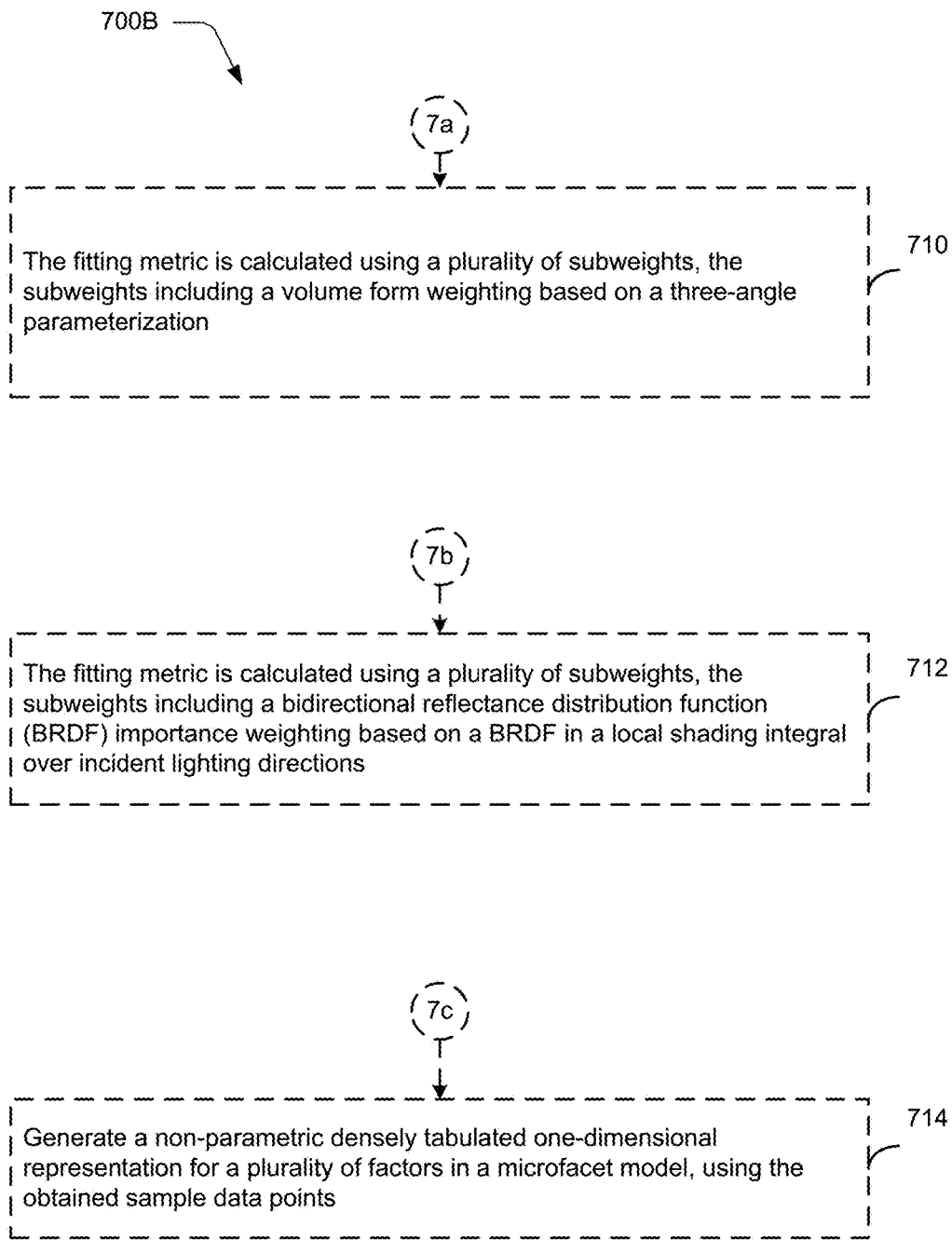

FIGS. 7A-7B are a flowchart illustrating example operations of the system of FIG. 3, according to example embodiments. In the example of FIG. 7A, a plurality of measured sample data points associated with reflectance on a surface of a material may be obtained (702).

The measured sample data points be fitted to a model by applying a fitting metric to the obtained sample data points, the fitting metric calculated using a sum-of-squares weighting, the sum-of-squares weighting including a non-constant function of measurement magnitudes of the obtained plurality of measured sample data points (704).

For example, the sum-of-squares weighting may include squared differences between predictions of the model and actual measurement values (706).

For example, obtaining the plurality of measured sample data points may include obtaining the plurality of measured sample data points representing measurements of an appearance of brightness of points on the surface (708).

For example, the fitting metric may be calculated using a plurality of subweights, the subweights including a volume form weighting based on a three-angle parameterization (710), in the example of FIG. 7B.

For example, the fitting metric may be calculated using a plurality of subweights, the subweights including a bidirectional reflectance distribution function (BRDF) importance weighting based on a BRDF in a local shading integral over incident lighting directions (712).

For example, a non-parametric densely tabulated one-dimensional representation for a plurality of factors in a microfacet model may be generated, using the obtained sample data points (714).

IV. Derivation of Isotropic BRDF Parameterization

Generally, a spherical coordinate system is a coordinate system for three-dimensional space where the position of a point is specified by three values: the radial distance of that point from a fixed origin, its polar angle measured from a fixed zenith direction, and the azimuth angle of its orthogonal projection on a reference plane that passes through the origin and is orthogonal to the zenith, measured from a fixed reference direction on that plane.

Thus, an azimuth may be an angular measurement in a spherical coordinate system. The vector from an observer (origin) to a point of interest may be projected perpendicularly onto a reference plane; the angle between the projected vector and a reference vector on the reference plane may be referred to as the azimuth.

In this derivation, a canonical coordinate system is assumed with normal surface normal n=z=(0,0,1) and halfway vector h in the zx-plane; i.e., perpendicular to y=(0,1,0). In other words, the azimuthal angle of the halfway vector is $\phi_h$=0.

Then the halfway direction can be parameterized by $\theta_h \in [0, \pi/2]$ $$h = z \cos \theta_h + x \sin \theta_h \quad (43)$$

and a perpendicular direction (also in the zx-plane) by $$h^\perp = z \sin \theta_h - x \cos \theta_h \quad (44)$$

To complete this orthonormal coordinate frame:

$$h^* = h \times h^\perp = -y \quad (45)$$

Then the light direction is $$i = h \cos \theta_d + (h^\perp \cos \phi_d + h^* \sin \phi_d) \sin \theta_d \quad (46)$$

and the view direction is $$o = h \cos \theta_d - (h^\perp \cos \phi_d + h^* \sin \phi_d) \sin \theta_d \quad (47)$$

parameterized by $\theta_d \in [0,\pi/2]$ and $\phi_d \in [0, \pi]$ (which eliminates redundant reciprocal pairs). It is noted that the labeling of the two directions as "input" and "output" may be switched due to reciprocity. Writing the components out fully yields $i_x = \sin\theta_h \cos\theta_d - \cos\theta_h \cos\phi_d \sin\theta_d$ $i_y = -\sin\phi_d \sin\theta_d$ $i_z = \cos\theta_h \cos\theta_d + \sin\theta_h \cos\phi_d \sin\theta_d$ $o_x = \sin\theta_h \cos\theta_d + \cos\theta_h \cos\phi_d \sin\theta_d$ $o_y = \sin\phi_d \sin\theta_d$ $o_z = \cos\theta_h \cos\theta_d - \sin\theta_h \cos\phi_d \sin\theta_d$ (48)

Thus, the cosines of the elevation angles for the in/out directions are $\cos\theta_i = i_z = \cos\theta_h \cos\theta_d + \sin\theta_h \cos\phi_d \sin\theta_d$ $\cos\theta_o = o_z = \cos\theta_h \cos\theta_d - \sin\theta_h \cos\phi_d \sin\theta_d$ (49)

and the tangents of the azimuthal angles are $$\tan\phi_i = \frac{i_y}{i_x} = \frac{-\sin\phi_d \sin\theta_d}{\sin\theta_h \cos\theta_d - \cos\theta_h \cos\phi_d \sin\theta_d}$$ (50)

$$\tan\phi_o = \frac{o_y}{o_x} = \frac{\sin\phi_d \sin\theta_d}{\sin\theta_h \cos\theta_d + \cos\theta_h \cos\phi_d \sin\theta_d}$$

To perform the inverse map, the halfway vector may be first computed as:

$h = (i+o)/\|i+o\|$ (51)

which lies in the zx-plane (have 0 y component). Then $h^\perp = (-h_z, 0, h_x)$ (52)

Thus, the original parametric angles may be inferred via:

$\cos\theta_h = h_z$ (53)

$\cos\theta_d = i \cdot h = o \cdot h$ $\sin\theta_d = \sqrt{1 - \cos^2\theta_d}$ $\cos\phi_d = \dfrac{i \cdot h^\perp}{\sin\theta_d}$ $\sin\phi_d = \dfrac{i \cdot h^*}{\sin\theta_d} = \dfrac{-i_y}{\sin\theta_d}$ In the general case, the azimuthal angle of the halfway vector is not 0; i.e. $\phi_h \neq 0$. To convert from parametric coordinates to in/out directions involves an additional rotation of both i and o around z via the 3D rotation:

$$R(\phi_h) = \begin{bmatrix} \cos\phi_h & -\sin\phi_h & 0 \\ \sin\phi_h & \cos\phi_h & 0 \\ 0 & 0 & 1 \end{bmatrix}$$ (54)

To convert to parametric coordinates from general in/out directions, one may first determine:

$$\phi_h = \tan^{-1}\left(\frac{h_y}{h_x}\right)$$ (55)

and then rotate the in/out directions by the inverse of the matrix above: $R^T(\phi_h)$. This may ensure the halfway vector lies in the zx-plane and the previous formulae in Equation (53) apply.

V. Derivation of Parametric Weighting for an Isotropic BRDF

As derived above, an isotropic BRDF may be parameterized by three angles: $\theta_h$, $\theta_d$, and $\phi_d$, which determine the in (light) and out (view) directions via $i_x = \sin\theta_h \cos\theta_d - \cos\theta_h \cos\phi_d \sin\theta_d$ $i_y = -\sin\phi_d \sin\theta_d$ $i_z = \cos\theta_h \cos\theta_d + \sin\theta_h \cos\phi_d \sin\theta_d$ $o_x = \sin\theta_h \cos\theta_d + \cos\theta_h \cos\phi_d \sin\theta_d$ $o_y = \sin\phi_d \sin\theta_d$ $o_z = \cos\theta_h \cos\theta_d - \sin\theta_h \cos\phi_d \sin\theta_d$ (56)

Let $T(\theta_h, \theta_d, \phi_d)$ denote the above transformation that goes from $(\theta_h, \theta_d, \phi_d)$ parameter space (3D input space) to (i, o) output space (6D input space). Then the volume form, $d\Omega$, induced by the above parameterization may be denoted as:

$d\Omega = \sqrt{\det(\partial T^T \partial T)} d\theta_h d\theta_d d\phi_d$ (57)

where $\partial T$ is the (6×3) Jacobian of the transformation T. The product $g = \partial T^T \partial T$ is the (3×3) metric tensor of the transformation, and the square root of its determinant scales the volume form after a coordinate transformation.

Taking derivatives and evaluating:

$$g = \begin{bmatrix} 2(\cos^2\theta_d + \sin^2\theta_d \cos^2\phi_d) & 0 & 0 \\ 0 & 2 & 0 \\ 0 & 0 & 2\sin^2\theta_d \end{bmatrix}$$ (58)

and so $d\Omega = \sqrt{\det g}\, d\theta_h d\theta_d d\phi_d = \sqrt{8\sin^2\theta_d(\cos^2\theta_d + \sin^2\theta_d \cos^2\phi_d)}\, d\theta_h d\theta_d d\phi_d$ (59)

It is noted that this does not depend on $\theta_h$.

If the parameterization is in terms of $\theta_h' = \sqrt{\theta_h}$ rather than $\theta_h$ itself, then $d\theta_h = 2\theta_h' d\theta_h'$ (60)

The differential volume may be evaluated at the center of each parameterization bin, or for more accuracy, may be averaged over the whole bin via numerical integration.

Further, the importance of the BRDF sample may also be multiplied by $w = \max(0, \cos\theta_i)\max(0, \cos\theta_o) = \max(0, i_z)\max(0, \cos o_z)$ (61)

since the power of light reflected to the observer per unit area on the surface depends on these factors.

VI. Aspects of Certain Embodiments

Features discussed herein are provided as example embodiments that may be implemented in many different ways that may be understood by one of skill in the art of data processing, without departing from the spirit of the discussion herein. Such features are to be construed only as example embodiment features, and are not intended to be construed as limiting to only those detailed descriptions.

For example, a system includes an apparatus that includes a computer-readable storage medium storing executable code, the executable code including a reflectance representation manager that includes a data acquisition module that obtains a plurality of measured sample data points associated with reflectance on a surface of a material. A representation generator generates a non-parametric densely tabulated one-dimensional representation for a plurality of factors in a microfacet model, using the obtained sample data points.

A representation generator generates a non-parametric densely tabulated one-dimensional representation for a plurality of factors in a microfacet model, using the obtained sample data points.

Obtaining the plurality of measured sample data points includes obtaining the plurality of measured sample data points representing measurements of an appearance of brightness of points on the surface.

Obtaining the plurality of measured sample data points includes obtaining the plurality of measured sample data points representing measurements of an appearance of brightness of points on the surface, based on the brightness perceived under a plurality of different views and light positions.

The representation generator generates the non-parametric densely tabulated one-dimensional representation using a fitting metric that is calculated using a sum-of-squares weighting, wherein the weighting includes a non-constant function of measurement magnitudes of the obtained plurality of measured sample data points.

The fitting metric is minimized using an alternating weighted least squares (AWLS) numerical technique.

The representation generator generates the non-parametric densely tabulated one-dimensional representation using three one-dimensional functions that are factors in the microfacet model, using the obtained sample data points.

The factors include a Fresnel factor (F) that represents a dependence of the reflectance on a spread angle $\theta_d$, a normal distribution function (D) that is a probability distribution function representing a probability that a microfacet normal makes an angle of $\theta_h$ with a surface macro-scale normal, and a geometric factor (G) that represents a micro-geometry shadowing and inter-reflecting light onto the micro-geometry itself, as a function of one or more of an obliquity of a light direction or an obliquity of a view direction.

The representation generator generates the non-parametric densely tabulated one-dimensional representation by applying the microfacet model independently for each color channel of a measurement spectrum.

The representation generator generates the non-parametric densely tabulated one-dimensional representation by applying the microfacet model independently as a three-channel measurement each of a red channel, a green channel, and a blue channel, for an RGB (red-green-blue) measurement spectrum.

For example, a plurality of measured sample data points associated with reflectance on a surface of a material are obtained. The measured sample data points are fitted to a model by applying a model fitting metric to the obtained sample data points, the model fitting metric calculated using a nonnegative, nonzero power of a ratio of a first function and a second function, the first and second functions defined over normalized values of the plurality of measured sample data points, the first function defined as a compressive function, the second function defined as a non-asymptotically increasing function.

The obtained plurality of measured sample data points includes a plurality of measured sample data points representing reflectance on a surface of a material.

The model fitting metric includes a volume form weighting based on a three-angle parameterization.

The model fitting metric includes a bidirectional reflectance distribution function (BRDF) importance weighting based on a BRDF in a local shading integral over incident lighting directions.

The model fitting metric is minimized using an alternating weighted least squares (AWLS) numerical technique.

The measured sample data points include a measured sample of high dynamic range (HDR) data points that include a set of data points having values greater than a predetermined threshold.

For example, a plurality of measured sample data points associated with reflectance on a surface of a material are obtained. The measured sample data points are fitted to a model by applying a fitting metric to the obtained sample data points, the fitting metric calculated using a sum-of-squares weighting, the sum-of-squares weighting including a non-constant function of measurement magnitudes of the obtained plurality of measured sample data points.

The sum-of-squares weighting includes squared differences between predictions of the model and actual measurement values.

Obtaining the plurality of measured sample data points includes obtaining the plurality of measured sample data points representing measurements of an appearance of brightness of points on the surface.

The fitting metric is calculated using a plurality of subweights, the subweights including a volume form weighting based on a three-angle parameterization.

The fitting metric is calculated using a plurality of subweights, the subweights including a bidirectional reflectance distribution function (BRDF) importance weighting based on a BRDF in a local shading integral over incident lighting directions.

A non-parametric densely tabulated one-dimensional representation for a plurality of factors in a microfacet model is generated, using the obtained sample data points.

One skilled in the art of data processing will understand that there may be many ways of determining reflectance representations, without departing from the spirit of the discussion herein.

Customer privacy and confidentiality have been ongoing considerations in data processing environments for many years. Thus, example techniques for determining reflectance representations may use user input and/or data provided by users who have provided permission via one or more subscription agreements (e.g., "Terms of Service" (TOS) agreements) with associated applications or services associated with such techniques. For example, users may provide consent to have their input/data transmitted and stored on devices, though it may be explicitly indicated (e.g., via a user accepted agreement) that each party may control how transmission and/or storage occurs, and what level or duration of storage may be maintained, if any. Further, identifiers that may be used to identify devices used by a user may be obfuscated, e.g., by hashing actual user information. It is to be understood that any user input/data may be obtained in accordance with the privacy laws and regulations of any relevant jurisdiction.

Implementations of the various techniques described herein may be implemented in digital electronic circuitry, or in computer hardware, firmware, software, or in combinations of them (e.g., an apparatus configured to execute instructions to perform various functionality).

Implementations may be implemented as a computer program embodied in signals (e.g., a pure signal such as a pure propagated signal). Such implementations will be referred to herein as implemented via a "computer-readable transmission medium," which does not qualify herein as a "computer-readable storage medium" or a "computer-readable storage device" as discussed below.

Alternatively, implementations may be implemented via a machine usable or machine readable storage device (e.g., a magnetic or digital medium such as a Universal Serial Bus (USB) storage device, a tape, hard disk drive, compact disk (CD), digital video disk (DVD), etc.), storing executable instructions (e.g., a computer program), for execution by, or to control the operation of, a computing apparatus (e.g., a data processing apparatus), e.g., a programmable processor, a special-purpose processor or device, a computer, or multiple computers. Such implementations may be referred to herein as implemented via a "computer-readable storage medium" or a "computer-readable storage device" and are thus different from implementations that are purely signals such as pure propagated signals (and thus do not qualify herein as a "computer-readable transmission medium" as discussed above). Thus, as used herein, a reference to a "computer-readable storage medium" or a "computer-readable storage device" specifically excludes signals (e.g., propagated signals) per se.

A computer program, such as the computer program(s) described above, can be written in any form of programming language, including compiled, interpreted, or machine languages, and can be deployed in any form, including as a stand-alone program or as a module, component, subroutine, or other unit suitable for use in a computing environment. The computer program may be tangibly embodied as executable code (e.g., executable instructions) on a machine usable or machine readable storage device (e.g., a computer-readable medium). A computer program that might implement the techniques discussed above may be deployed to be executed on one computer or on multiple computers at one site or distributed across multiple sites and interconnected by a communication network.

Method steps may be performed by one or more programmable processors executing a computer program to perform functions by operating on input data and generating output. The one or more programmable processors may execute instructions in parallel, and/or may be arranged in a distributed configuration for distributed processing. Example functionality discussed herein may also be performed by, and an apparatus may be implemented, at least in part, as one or more hardware logic components. For example, and without limitation, illustrative types of hardware logic components that may be used may include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Processors suitable for the execution of a computer program include, by way of example, both general and special purpose microprocessors, and any one or more processors of any kind of digital computer. Generally, a processor will receive instructions and data from a read only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT), liquid crystal display (LCD), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback. For example, output may be provided via any form of sensory output, including (but not limited to) visual output (e.g., visual gestures, video output), audio output (e.g., voice, device sounds), tactile output (e.g., touch, device movement), temperature, odor, etc.

Further, input from the user can be received in any form, including acoustic, speech, or tactile input. For example, input may be received from the user via any form of sensory input, including (but not limited to) visual input (e.g., gestures, video input), audio input (e.g., voice, device sounds), tactile input (e.g., touch, device movement), temperature, odor, etc.

Further, a natural user interface (NUI) may be used to interface with a user. In this context, a "NUI" may refer to any interface technology that enables a user to interact with a device in a "natural" manner, free from artificial constraints imposed by input devices such as mice, keyboards, remote controls, and the like.

Examples of NUI techniques may include those relying on speech recognition, touch and stylus recognition, gesture recognition both on a screen and adjacent to the screen, air gestures, head and eye tracking, voice and speech, vision, touch, gestures, and machine intelligence. Example NUI technologies may include, but are not limited to, touch sensitive displays, voice and speech recognition, intention and goal understanding, motion gesture detection using depth cameras (e.g., stereoscopic camera systems, infrared camera systems, RGB (red, green, blue) camera systems and combinations of these), motion gesture detection using accelerometers/gyroscopes, facial recognition, 3D displays, head, eye, and gaze tracking, immersive augmented reality and virtual reality systems, all of which may provide a more natural interface, and technologies for sensing brain activity using electric field sensing electrodes (e.g., electroencephalography (EEG) and related techniques).

Implementations may be implemented in a computing system that includes a back end component, e.g., as a data server, or that includes a middleware component, e.g., an application server, or that includes a front end component, e.g., a client computer having a graphical user interface or a Web browser through which a user can interact with an implementation, or any combination of such back end, middleware, or front end components. Components may be interconnected by any form or medium of digital data communication, e.g., a communication network. Examples of communication networks include a local area network (LAN) and a wide area network (WAN), e.g., the Internet.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A system comprising:
   at least one processor; and
   a computer-readable storage medium that stores executable code which, when executed by the at least one processor, causes the at least one processor to:
   obtain measured three-dimensional (3D) sample data associated with reflectance on a surface of an isotropic material;
   fit the 3D sample data to a microfacet model comprising one-dimensional (1D) functions that are factors in the microfacet model by iteratively updating an individual factor while holding the remaining factors constant to generate a non-parametric densely tabulated 1D representation of the reflectance; and
   render one or more images using the non-parametric densely tabulated 1D representation.

2. The system of claim 1, wherein
   the measured 3D sample data represent measurements of an appearance of brightness of points on the surface of the isotropic material.

3. The system of claim 2, wherein:
   the appearance of brightness is based at least on brightness perceived under different views and light positions relative to the surface of the isotropic material.

4. The system of claim 1, wherein the executable code further causes the at least one processor to:
   fit the 3D sample data to the microfacet model using a fitting metric that is calculated using a sum-of-squares weighting, wherein the sum-of-squares weighting includes applying a non-constant function of measurement magnitudes of the measured 3D sample data.

5. The system of claim 4, wherein the executable code further causes the at least one processor to:
   minimize the fitting metric using an alternating weighted least squares (AWLS) numerical technique.

6. The system of claim 1, wherein the 1D functions of that are the factors in the microfacet model include three 1D functions corresponding to three dimensions of the measured 3D sample data.

7. The system of claim 6, wherein:
   the factors include:
   a Fresnel factor (F) that represents a dependence of the reflectance on a spread angle $\theta_d$,
   a normal distribution function (D) representing a probability that a microfacet normal makes an angle of $\theta_h$ with a surface macro-scale normal, and
   a geometric factor (G) that represents a micro-geometry shadowing and inter-reflecting light onto the micro-geometry itself, as a function of one or more of an obliquity of a light direction or an obliquity of a view direction.

8. The system of claim 1, wherein the executable code further causes the at least one processor to:
   generate the non-parametric densely tabulated 1D representation by applying the microfacet model independently for each color channel of a measurement spectrum.

9. The system of claim 1, wherein the executable code further causes the at least one processor to:
   generate the non-parametric densely tabulated 1D representation by applying the microfacet model independently as a three-channel measurement each of a red channel, a green channel, and a blue channel, for an RGB (red-green-blue) measurement spectrum.

10. A computer-implemented method comprising:
    obtaining measured three-dimensional (3D) sample data associated with reflectance on a surface of an isotropic material;
    fitting the measured 3D sample data to a model that includes one-dimensional (1D) functions to generate a 1D representation of the model, the fitting including applying a model fitting metric to the measured 3D sample data, the model fitting metric calculated using a nonnegative, nonzero power of a ratio of a compressive function and a non-asymptotically increasing function, the compressive function and the non-asymptotically increasing function defined over normalized values of the measured 3D sample data; and
    rendering one or more images based at least on the 1D representation of the model.

11. The method of claim 10, wherein:
    the model fitting metric includes a volume form weighting based at least on a three-angle parameterization corresponding to three dimensions of the measured 3D sample data.

12. The method of claim 10, wherein:
    the model fitting metric includes a bidirectional reflectance distribution function (BRDF) importance weighting based at least on a BRDF in a local shading integral over incident lighting directions.

13. The method of claim 10, further comprising:
    minimizing the model fitting metric using an alternating weighted least squares (AWLS) numerical technique.

14. The method of claim 10, wherein:
    the measured 3D sample data include high dynamic range (HDR) data points with values greater than a predetermined threshold.

15. A system comprising:
    at least one data processing apparatus; and
    a computer-readable storage medium storing executable code which, when executed by the at least one data processing apparatus, causes the at least one data processing apparatus to:
    obtain measured three dimensional (3D) sample data associated with reflectance on a surface of an isotropic material;
    fit the measured 3D sample data to a model that includes 1D functions to generate a one-dimensional (1D) representation of the model by applying a fitting metric to the measured 3D sample data, the fitting metric calculated using a sum-of-squares weighting, the sum-of-squares weighting including a non-constant function of measurement magnitudes of the measured 3D sample data; and
    render one or more images using the 1D representation.

16. The system of claim 15, wherein:
the sum-of-squares weighting includes squared differences between predictions of the model and actual measurement values.

17. The system of claim 15, wherein:
the measured 3D sample data represent an appearance of brightness of points on the surface of the isotropic material.

18. The system of claim 15, wherein the executable code further causes the at least one data processing apparatus to:
calculate the fitting metric using a plurality of subweights, the plurality of subweights including a volume form weighting based at least on a three-angle parameterization corresponding to three dimensions of the measured 3D sample data.

19. The system of claim 15, wherein the executable code further causes the at least one data processing apparatus to:
calculate the fitting metric using a plurality of subweights, the plurality of subweights including a bidirectional reflectance distribution function (BRDF) importance weighting based at least on a BRDF in a local shading integral over incident lighting directions.

20. The system of claim 15, wherein:
the 1D representation is a non-parametric densely tabulated 1D representation for the 1D functions in the model.

* * * * *